United States Patent
Wang

(10) Patent No.: US 11,168,046 B2
(45) Date of Patent: Nov. 9, 2021

(54) 1,3-FATTY DIOL COMPOUNDS AND DERIVATIVES THEREOF

(71) Applicant: Genomatica, Inc., San Diego, CA (US)

(72) Inventor: Haibo Wang, San Pablo, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 16/739,645

(22) Filed: Jan. 10, 2020

(65) Prior Publication Data

US 2020/0385325 A1 Dec. 10, 2020

Related U.S. Application Data

(63) Continuation of application No. 15/705,012, filed on Sep. 14, 2017, now Pat. No. 10,570,074.

(60) Provisional application No. 62/394,537, filed on Sep. 14, 2016.

(51) Int. Cl.
*C07C 33/035* (2006.01)
*C07H 15/10* (2006.01)

(52) U.S. Cl.
CPC ........... *C07C 33/035* (2013.01); *C07H 15/10* (2013.01)

(58) Field of Classification Search
None
See application file for complete search history.

(56) References Cited

U.S. PATENT DOCUMENTS

| | | | |
|---|---|---|---|
| 9,163,267 B2 | 10/2015 | Del Cardayre | |
| 9,353,090 B2 | 5/2016 | Brenneman et al. | |
| 9,382,189 B2 | 7/2016 | Dubois et al. | |
| 2014/0275506 A1 | 9/2014 | Littich et al. | |

FOREIGN PATENT DOCUMENTS

| | | |
|---|---|---|
| CN | 105218603 A | 1/2016 |
| JP | 2007508300 A | 4/2007 |
| WO | 2006011430 A1 | 2/2006 |
| WO | WO-2016/011430 A1 | 1/2016 |

OTHER PUBLICATIONS

Office Action issued in Corresponding Mexican Application No. MX/a/2019/002913 dated Oct. 1, 2020.
El-Sukkary, et al., "Synthesis and Characterization of some Alkyl Polyglycosides Surfactants," J Surface Deterg 11: 129-137 (2008).
Donohoe et al., "Osmium-Mediated Oxidative Cyclizations: A Study into the Range of Initiators That Facilitate Cyclization," Chem. Asian Journal, 2009, pp. 1237-1247 (11 pages).
International Search Report issued in International Application No. PCT/US2017/051664 dated Nov. 2, 2017 (5 pages).
Non-Final Rejection in U.S. Appl. No. 15/705,012 dated Jan. 24, 2019.
Notice of Allowance in U.S. Appl. No. 15/705,012 dated Oct. 11, 2019.
Examination Report issued in corresponding Indian Application No. 201917011120 dated Dec. 11, 2020.
Extended European Search Report issued in corresponding European Application No. 20189079.5 dated Dec. 23, 2020.
Office Action from corresponding Indonesia Application No. P00201903036 dated Feb. 25, 2021.

*Primary Examiner* — Ana Z Muresan
(74) *Attorney, Agent, or Firm* — Harness Dickey & Pierce P.L.C.

(57) ABSTRACT

The disclosure relates to the field of specialty chemicals. In particular, the disclosure provides novel 1,3-fatty-diol compounds and derivatives thereof which are useful e.g., in the production of personal care products, surfactants, detergents, polymers, paints, coatings, and as emulsifiers, emollients, and thickeners in cosmetics and foods, as industrial solvents and plasticizers, etc.

16 Claims, 4 Drawing Sheets

1,3-FATTY DIOL COMPOUNDS AND DERIVATIVES THEREOF

CROSS REFERENCE TO RELATED APPLICATIONS

This application is a continuation of U.S. patent application Ser. No. 15/705,012, filed Sep. 14, 2017, which claims the benefit of U.S. Provisional Application No. 62/394,537 filed, Sep. 14, 2016, which are herein incorporated by reference in their entireties.

FIELD

The disclosure relates generally to the field of specialty chemicals suitable for use as components of industrial agents and processes, e.g., in the production of detergents and surfactants, as emulsifiers, emollients, and thickeners in cosmetics and foods, as industrial solvents and plasticizers, etc.

BACKGROUND

Fatty-alcohols, particularly fatty-diols (or aliphatic diols) are amphipathic molecules having many commercial and industrial uses. For example, fatty alcohols find use as emollients and thickeners in cosmetics and foods and as industrial solvents, plasticizers, lubricants, emulsifiers, building blocks of polymers, etc., (see e.g., H. Maag (1984) Journal of the American Oil Chemists' Society 61(2): 259-267). Of particular usefulness are the 1,3-fatty-diols.

1,3-fatty-diols are useful as lubricants, as linking molecules between other molecules e.g., example in the production of polymers. 1,3-fatty diols are also useful as surfactants and as precursors to surfactants, for example, 1,3-fatty diols can be used to prepare "Gemini" surfactants in which both alcohol moieties are chemically modified (e.g., ethoxylated, glycosylated, sulfated, etc.). Gemini surfactants, or Gemini-like surfactants exhibit superior properties compared to those of analogous conventional surfactants (see, e.g., *Gemini Surfactants: Synthesis, Interfacial and Solution-Phase Behavior, and Applications*, Vol. 117, Zana, R.; Xia, J., Eds.; Marcel Dekker: New York, 2004).

The 3-hydroxy moiety of 1,3-fatty-diols forms a chiral center at the third carbon (C-3) which makes 1,3-fatty-diols useful as synthons for the production of chirally important compounds such as pharmaceuticals, nutraceuticals, pesticides, herbicides, flavors, fragrances, solvents, bioactive compounds, etc.

In addition to the functionality of the hydroxyl groups, variations in the structure of the carbon chain of 1,3-fatty diols provide molecules with additional chemistries and/or potentially new properties that can be used to address old problems in an improved way and/or which can find new uses altogether. For example, unsaturated fatty diols have additional functional groups in the form of double bonds which are available for chemical reactions.

Unsaturated fatty alcohols and fatty-diols are particularly valued because the presence of the double bond contributes a number of favorable properties on the molecule. For example, compared to their saturated counterparts, unsaturated fatty diols have lower melting point, higher solubility in water and offer the possibility of introducing functional groups into the C=C double bond (Egan, R., et al., (1984) Journal of the American Oil Chemists' Society, Vol. 61 (2): 324-329). Thus, unsaturated fatty alcohols are important intermediates for a large number of products of the chemical industry (see e.g., U. Ploog et al. in Seifen-Öle-Fette-Wachse 109, 225 (1983)).

Unlike saturated fatty-diols, which are readily produced from petroleum precursors using e.g., the Prins reaction (see e.g., E. Arundale, L. A. Mikeska Chem. Rev.; 1952; 51(3); 505-555) unsaturated fatty diols are much more difficult to produce from petrochemical materials and processes.

Typically, unsaturated fatty alcohols are produced by subjecting fatty acid methyl ester mixtures derived from oils such as e.g., sunflower, palm, palm kernel and coconut to high-pressure hydrogenation in the presence of chromium- and/or zinc-containing mixed oxide catalysts (see e.g., Ullmann's Encyclopedia of Industrial Chemistry $7^{th}$ Edition, Vol. 14: 117. John Wiley and Sons, Inc. 2011). The zinc chromite type catalysts promote selective hydrogenation of the carbonyl group instead of the C=C double bond (see e.g., Adkins and Sauer, (1937) Journal of the American Chemical Society, Vol. 59 (1):1-3).

Unfortunately, because unsaturated fatty alcohols and unsaturated fatty-diols are produced only from limited numbers of natural oils, the supply of raw materials can be volatile and variable. Additionally, the reliance on natural oils and their inherent structures for the production of fatty diols limits the variety of chemical structures that can be produced.

Clearly then, since 1,3-fatty diols and especially, unsaturated 1,3-fatty-diols, are such useful molecules, what is needed in the art are new 1,3-fatty-diols.

Fortunately, as will be clear from the detailed description that follows, the present disclosure provides for this and other needs.

SUMMARY

One aspect of the disclosure provides a 12-carbon, unbranched, unsaturated fatty-diol having a single Δ5 double bond and having a hydroxy group at carbon number one (C-1) and having a hydroxy group at carbon number 3 (C-3), wherein a chiral center exists at C-3, and wherein the fatty-diol has a generic chemical formula according to Formula II.

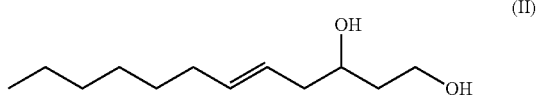

(II)

In one exemplary embodiment, the double bond is in (Z) configuration. In another exemplary embodiment, the double bond is in (E) configuration. In one exemplary embodiment, the chiral center at C-3 has an R configuration. In one exemplary embodiment, the chiral center at C-3 has an S configuration. In another exemplary embodiment, the double bond is in (Z) configuration and the chiral center at C-3 has an R configuration.

One aspect of the disclosure provides a 14-carbon, unbranched, unsaturated fatty-diol having a single Δ7 double bond and having a hydroxy group at carbon number one (C-1) and having a hydroxy group at carbon number 3 (C-3), wherein a chiral center exists at C-3, and wherein the fatty-diol has a generic chemical formula according to Formula III.

(II)

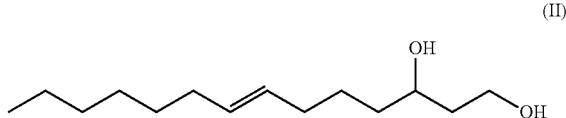 [SMILES: CCCCCC/C=C/CCCC(O)CCO]

In one exemplary embodiment, the double bond is in (Z) configuration. In another exemplary embodiment, the double bond is in (E) configuration. In one exemplary embodiment, the chiral center at C-3 has an R configuration. In one exemplary embodiment, the chiral center at C-3 has an S configuration. In another exemplary embodiment, the double bond is in (Z) configuration and the chiral center at C-3 has an R configuration.

One aspect of the disclosure provides a 16-carbon, unbranched, unsaturated fatty-diol having a single Δ9 double bond and having a hydroxy group at carbon number one (C-1) and having a hydroxy group at carbon number 3 (C-3), wherein a chiral center exists at C-3, and wherein the fatty-diol has a chemical formula according to Formula IV (IV)

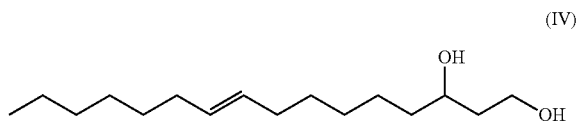 [SMILES: CCCCCC/C=C/CCCCCC(O)CCO]

In one exemplary embodiment, the double bond is in (Z) configuration. In another exemplary embodiment, the double bond is in (E) configuration. In one exemplary embodiment, the chiral center at C-3 has an R configuration. In one exemplary embodiment, the chiral center at C-3 has an S configuration. In another exemplary embodiment, the double bond is in (Z) configuration and the chiral center at C-3 has an R configuration.

One aspect of the disclosure provides a 1,3-fatty-diol derivative having a chemical formula according to Formula V.

(V)

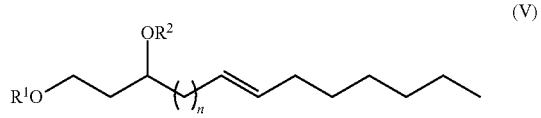

wherein n is an integer selected from 0, 1, 2, 3, 4, 5, 6, 7, 8, 9, 10, 11, 12, 13 and 14, and wherein $R^1$ and $R^2$ are each independently selected from the group consisting of H, a monosaccharide bound at an anomeric carbon of the monosaccharide, a disaccharide bound at an anomeric carbon of the disaccharide, a trisaccharide bound at an anomeric carbon, and a polysaccharide bound at an anomeric carbon. In one exemplary embodiment, $R^1$ and $R^2$ are not both H. In another exemplary embodiment, neither $R^1$ nor $R^2$ are H. In another exemplary embodiment, the monosaccharide is selected from pentose sugars and hexose sugars. In another exemplary embodiment, the hexose sugar selected from allose, altrose, glucose, mannose, gulose, iodose, galactose or talose. In another exemplary embodiment, the disaccharide, the trisaccharide, and the polysaccharide comprise sugars selected from pentose sugars, hexose sugars or a mixture of any two or more thereof. In another exemplary embodiment, the hexose sugar selected from allose, altrose, glucose, mannose, gulose, iodose, galactose, talose, or a mixture of any two or more thereof. In another exemplary embodiment, $R^1$ and $R^2$ are different monosaccharides. In another exemplary embodiment, $R^1$ and $R^2$ are the same monosaccharide. In another exemplary embodiment, the monosaccharide, the disaccharide, the trisaccharide, and the polysaccharide comprise a hexose sugar selected from allose, altrose, glucose, mannose, gulose, iodose, galactose, talose, or a mixture of any two or more thereof. In another exemplary embodiment, the monosaccharide, disaccharide, trisaccharide, or polysaccharide comprises a sugar selected from furanose sugars, pyranose sugars, or a mixture of any two or more thereof.

One aspect of the disclosure provides a 1,3-fatty-diol derivative having a chemical formula according to Formula VI.

(VI)

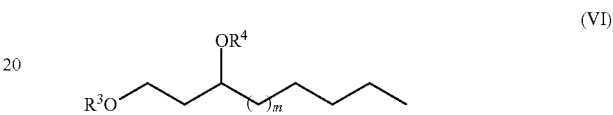

wherein m is an integer selected from 1, 2, 3, 4, 5, 6, 7, 8, 9, 10, 11, 12, 13, 14, 15, 16, 17 and 18 and wherein $R^3$ and $R^4$ are each independently selected from the group consisting of H, a monosaccharide bound at an anomeric carbon of the monosaccharide, a disaccharide bound at an anomeric carbon of the disaccharide, a trisaccharide bound at an anomeric carbon, and a polysaccharide bound at an anomeric carbon. In one exemplary embodiment, $R^3$ and $R^4$ are not both H. In another exemplary embodiment, neither $R^3$ nor $R^4$ are H. In another exemplary embodiment, the monosaccharide is selected from pentose sugars and hexose sugars. In another exemplary embodiment, the hexose sugar selected from allose, altrose, glucose, mannose, gulose, iodose, galactose or talose. In another exemplary embodiment, the disaccharide, the trisaccharide, and the polysaccharide comprise sugars selected from pentose sugars, hexose sugars or a mixture of any two or more thereof. In another exemplary embodiment, the hexose sugar selected from allose, altrose, glucose, mannose, gulose, iodose, galactose, talose, or a mixture of any two or more thereof. In another exemplary embodiment, $R^3$ and $R^4$ are different monosaccharides. In another exemplary embodiment, $R^3$ and $R^4$ are the same monosaccharide. In another exemplary embodiment, the monosaccharide, the disaccharide, the trisaccharide, and the polysaccharide comprise a hexose sugar selected from allose, altrose, glucose, mannose, gulose, iodose, galactose, talose, or a mixture of any two or more thereof. In another exemplary embodiment, the monosaccharide, disaccharide, trisaccharide, or polysaccharide comprises a sugar selected from furanose sugars, pyranose sugars, or a mixture of any two or more thereof.

DETAILED DESCRIPTION

Definitions

Figure 1A:
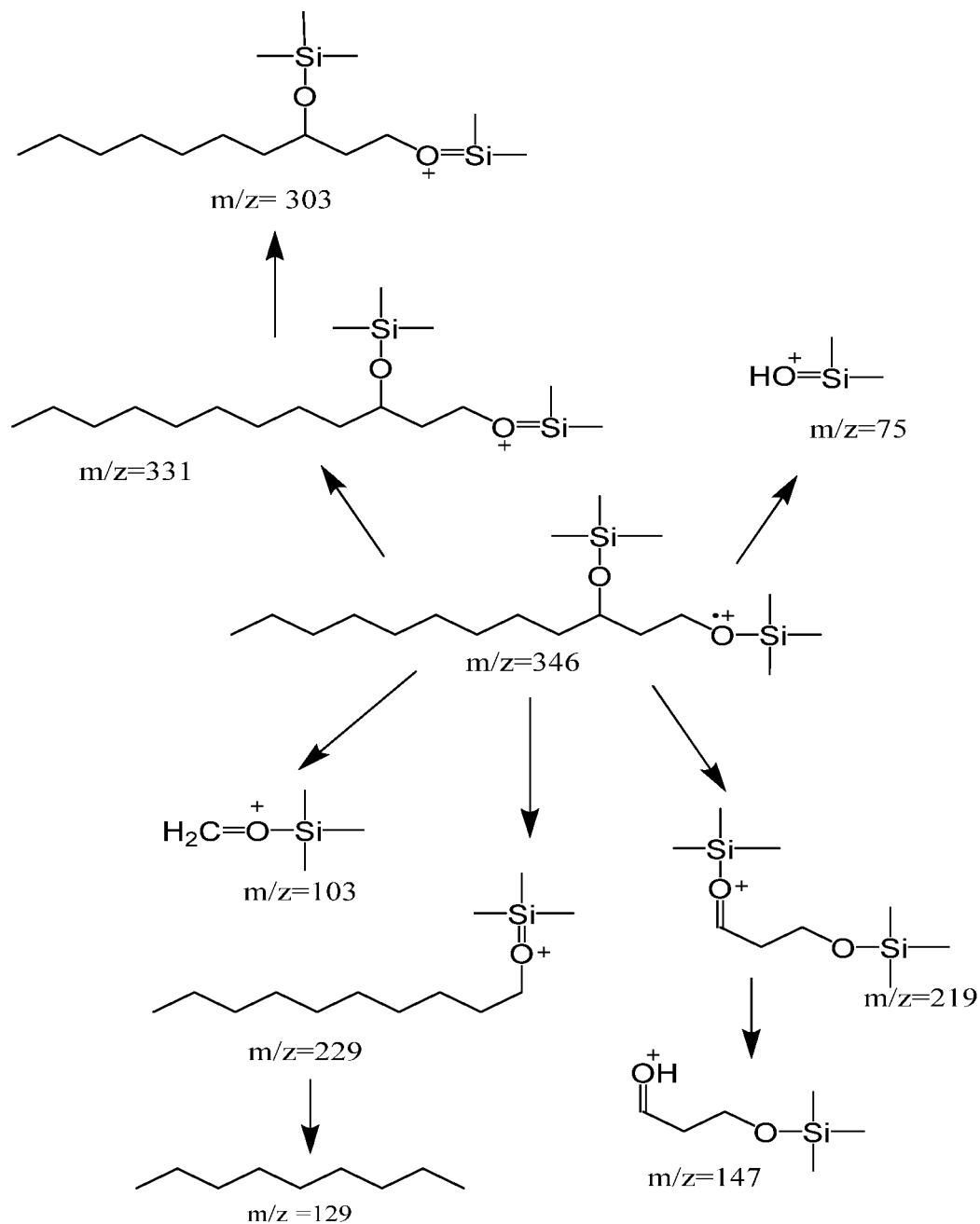
FIG. 1A Illustrates schematically the fragment ions formed from fragmentation of 1,3-dodecane diol trimethylsilyl ether.

As used herein and in the appended claims, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry. Basic texts disclosing the general terms in molecular biology and genetics include e.g., Lackie, *Dictionary of Cell and Molecular Biology*, Elsevier (5th ed. 2013). Basic texts disclosing the general methods and terms in biochemistry include e.g., *Lehninger Principles of Biochemistry* sixth edition, David L. Nelson and Michael M. Cox eds. W. H. Freeman (2012). Basic texts disclosing the general methods and terminology of fermentation include e.g., *Principles of Fermentation Technology*, 3rd Edition by Peter F Stanbury, Allan Whitaker and Stephen J Hall. Butterworth-Heinemann (2016). Basic texts disclosing the general methods and terms organic chemistry include e.g., Favre, Henri A. and Powell, Warren H. *Nomenclature of Organic Chemistry. IUPAC Recommendations and Preferred Name* 2013. Cambridge, UK: The Royal Society of Chemistry, 2013; *Practical Synthetic Organic Chemistry: Reactions, Principles, and Techniques*, Stephane Caron ed., John Wiley and Sons Inc. (2011); *Organic Chemistry*, 9th Edition—Francis Carey and Robert Giuliano, McGraw Hill (2013).

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as a mixture of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

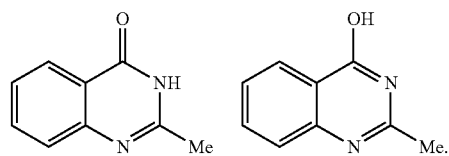

As another example, guanidines may exhibit the following isomeric forms in protic organic solution, also referred to as tautomers of each other:

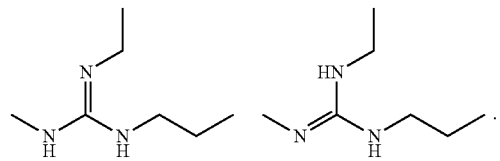

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Geometric isomers can be represented by the symbol which denotes a bond that can be a single, double or triple bond as described herein. Provided herein are various geometric isomers and mixtures thereof resulting from the arrangement of substituents around a carbon-carbon double bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

In certain embodiments, the pharmaceutically acceptable form thereof is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include cis- and trans-isomers, E- and Z-isomers, R- and S-enantiomers, diastereomers, (d)-isomers, (l)-isomers, racemic mixtures thereof, and other mixtures thereof, as falling within the scope of this disclosure.

"Enantiomers" are a pair of stereoisomers that are non-superimposable mirror images of each other. A mixture of a pair of enantiomers in any proportion can be known as a "racemic" mixture. The term "(+-)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared, for example, using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The term "fatty-diol" or "fatty diol" as used herein, refers to aliphatic di-alcohols having a carbon chain length of at least 5 carbons which comprise two hydroxy (—OH) groups covalently bound to the carbon chain. In exemplary embodiments, a "fatty diol" is a "1,3-fatty-diol". As used herein, the expression "1,3-fatty diol" refers to aliphatic di-alcohols having a carbon chain length of at least 8 carbons wherein the alcohol moieties are located at the first (C-1) and third carbons (C-3). "1,3-fatty-diols" may be saturated or unsaturated. Thus, in general as used herein, the expression "1,3-fatty-diol" refers to molecules having a structural formula as shown in Formula IA or Formula IB.

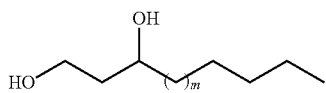
(IA)

In Formula IA, in is an integer selected from 1, 2, 3, 4, 5, 6, 7, 8, 9, 10, 11, 12, 13, 14, 15, 16, 17 and 18, and the C-3 carbon may be either an (R) or and (S) enantiomer.

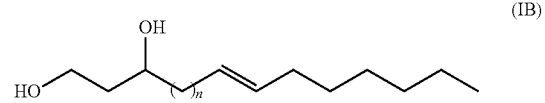
(IB)

In Formula IB, n is an integer selected from 0, 1, 2, 3, 4, 5, 6, 7, 8, 9, 10, 11, 12, 13 and 14, the double bond may be in either the (Z) or the (E) configuration and the C-3 carbon may be either an (R) or and (S) enantiomer. In exemplary embodiments, the 1,3 fatty-diol is 5-dodecene-1,3-diol. In other exemplary embodiments, the 1,3 fatty-diol is 9-hexadecene-1,3-diol.

The term "5-dodecene-1,3-diol" or equivalently "1,3-dodec-5-enediol" or equivalently "5-dodecen-1,3-diol" or equivalently "dodec-5-ene-1,3-diol" as used herein, refers to a novel 12-carbon, unbranched, unsaturated 1,3-diol having a double bond between the number 5 and number 6 carbons (i.e. a Δ5 double bond which can be in either the (Z) or (E) configuration) and having a hydroxy group at carbon number one (C-1) and having a hydroxy group at carbon number 3 (C-3), wherein a chiral center exists at C-3 and the C-3 carbon may be either an (R) or and (S) enantiomer. Such molecule has the generic structure shown in Formula II.

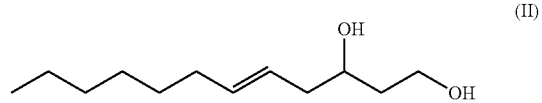
(II)

The term "7-tetradecene-1,3-diol" or equivalently "1,3-tetradec-7-enediol" or equivalently "7-tetradecen-1,3-diol" or equivalently "tetradec-7-ene-1,3-diol" as used herein, refers to a novel 14-carbon, unbranched, unsaturated 1,3-diol having a double bond between the number 7 and number 8 carbons (i.e. a Δ7 double bond which can be in either the (Z) or (E) configuration) and having a hydroxy group at carbon number one (C-1) and having a hydroxy group at carbon number 3 (C-3), wherein a chiral center exists at C-3 and the C-3 carbon may be either an (R) or and (S) enantiomer. Such molecule has the generic structure shown in Formula III.

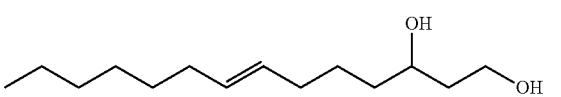
(III)

The term "9-hexadecene-1,3-diol" or equivalently "1,3-hexadec-9-enediol" or equivalently "9-hexadecen-1,3-diol" or equivalently "hexadec-9-ene-1,3-diol" as used herein, refers to a novel 16-carbon, unbranched, unsaturated 1,3-diol having a double bond between the number 9 and number 10 carbons (i.e. a Δ9 double bond which can be in either the (Z) or (E) configuration) and having a hydroxy group at carbon number one (C-1) and having a hydroxy group at carbon number 3 (C-3), wherein a chiral center exists at C-3 and the C-3 carbon may be either an (R) or and (S) enantiomer. Such molecule has the generic structure shown in Formula IV.

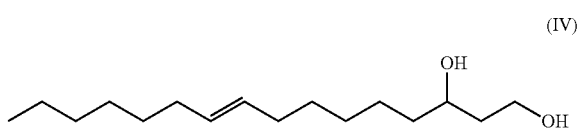 [SMILES: CCCCCC/C=C/CCCCCC(O)CCO]

(IV)

The term "polyol" as used herein, refers to compounds, typically fatty alcohols, which have more than one hydroxy group. Thus, as referred to herein, a polyol may have two hydroxy groups, three hydroxy groups, four hydroxy groups, etc. In general, a "polyol" that has two hydroxy groups is referred to herein as a "diol", a "polyol" that has three hydroxy groups is referred to herein as a "triol", a "polyol" that has four hydroxy groups is referred to herein as a "tetrol" and so on.

The expression "hydroxy group", "hydroxyl group", alcohol group" are used interchangeably herein and refer to a chemical functional group containing one oxygen atom covalently bonded to one hydrogen atom (—OH).

The term "enzyme classification (EC) number" refers to a number that denotes a specific polypeptide sequence or enzyme. EC numbers classify enzymes according to the reaction they catalyze. EC numbers are established by the nomenclature committee of the international union of biochemistry and molecular biology (IUBMB), a description of which is available on the IUBMB enzyme nomenclature website on the world wide web.

As used herein, the term "isolated," with respect to products (such as e.g., 5-dodecene-1,3-diol) refers to products that are separated from cellular components, cell culture media, or chemical or synthetic precursors.

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 97% free, at least at least about 98% free, at least about 99% free) from other components with which they are associated. As used herein, these terms also refer to the removal of contaminants from a sample. For example, the removal of contaminants can result in an increase in the percentage of fatty diols in a sample. For example, when a 1,3-diol is produced in a recombinant host cell, the 1,3-diol can be purified by the removal of host cell proteins. After purification, the percentage of 1,3-diols in the sample is increased. The terms "purify," "purified," and "purification" are relative terms which do not require absolute purity. Thus, for example, when a 1,3-diol is produced in recombinant host cells, a purified 1,3-diol is a 1,3-diol that is substantially separated from other cellular components (e.g., nucleic acids, polypeptides, lipids, carbohydrates, or other hydrocarbons).

I. 1,3-Fatty-Diol Compounds and Derivatives Thereof

A. General Methods

This disclosure utilizes routine techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); Current Protocols in Molecular Biology Volumes 1-3, John Wiley & Sons, Inc. (1994-1998).

This disclosure also utilizes routine techniques in the field of biochemistry. Basic texts disclosing the general methods and terms in biochemistry include e.g., *Lehninger Principles of Biochemistry* sixth edition, David L. Nelson and Michael M. Cox eds. W.H. Freeman (2012). This disclosure also utilizes routine techniques in industrial fermentation. Basic texts disclosing the general methods and terms in fermentation include e.g., *Principles of Fermentation Technology*, 3rd Edition by Peter F. Stanbury, Allan Whitaker and Stephen J. Hall. Butterworth-Heinemann (2016); *Fermentation Microbiology and Biotechnology*, 2nd Edition, E. M. T. El-Mansi, C. F. A. Bryce, Arnold L. Demain and A. R. Allman eds. CRC Press (2007). This disclosure also utilizes routine techniques in the field of organic chemistry. Basic texts disclosing the general methods and terms in organic chemistry include e.g., *Practical Synthetic Organic Chemistry: Reactions, Principles, and Techniques*, Stephane Caron ed., John Wiley and Sons Inc. (2011); *The Synthetic Organic Chemist's Companion*, Michael C. Pirrung, John Wiley and Sons Inc. (2007); *Organic Chemistry*, 9th Edition—Francis Carey and Robert Giuliano, McGraw Hill (2013).

B. 1,3-Fatty-Diols and Derivatives Thereof

As discussed supra, 1,3-fatty-diols are particularly useful molecules. In addition to providing two hydroxyl functional groups for reaction to form derivatives, the 3-hydroxy moiety of 1,3-fatty-diols forms a chiral center at the third carbon (C-3) which makes 1,3-fatty-diols useful as synthons for the production of chirally important compounds such as pharmaceuticals, nutraceuticals, pesticides, herbicides, flavors, fragrances, solvents, bioactive compounds, etc.

In addition to the functionality of the hydroxyl groups, variations in the structure of the carbon chain of 1,3-fatty diols provide molecules with additional chemistries and/or potentially new properties that can be used to address old problems in an improved way and/or which can find new uses altogether. For example, unsaturated fatty alcohols have additional functional groups in the form of double bonds which are available for chemical reactions.

Unsaturated fatty alcohols are particularly valued because the presence of the double bond contributes a number of favorable properties on the molecule. For example, compared to their saturated counterparts, unsaturated fatty alcohols have lower melting point, higher solubility in water and offer the possibility of introducing functional groups into the C=C double bond (Egan, R., et al., (1984) Journal of the American Oil Chemists' Society, Vol. 61 (2): 324-329). Thus, unsaturated fatty alcohols are important intermediates for a large number of products of the chemical industry (see e.g., U. Ploog et al. in Seifen-Ole-Fette-Wachse 109, 225 (1983)).

In an exemplary embodiment, the present disclosure provides novel unsaturated, unbranched 1,3-fatty-diols. In one exemplary embodiment, the novel unsaturated, unbranched 1,3-fatty-diol has the has the systematic name: 5-dodecene-1,3-diol or dodec-5-ene-1,3-diol. In some exemplary embodiments, the double bond is in (Z) configuration. In other exemplary embodiments, the double bond of 5-dodecene-1,3-diol is in (E) configuration. 5-dodecene-1, 3-diol has the generic structural Formula II.

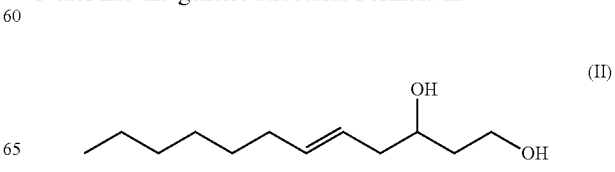

(II)

In Formula II the chiral C-3 carbon may be either the (R) enantiomer or the (S) enantiomer.

In another exemplary embodiment, the novel unsaturated, unbranched 1,3-fatty-diol has the has the systematic name: 7-hexadecene-1,3-diol or hexadec-7-ene-1,3-diol. In some exemplary embodiments, the double bond is in (Z) configuration. In other exemplary embodiments, the double bond is in (E) configuration. 7-hexadecene-1,3-diol has the generic structural Formula (III).

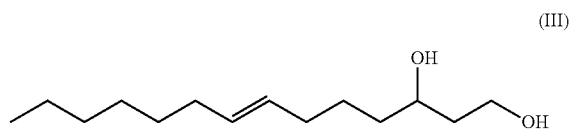 [SMILES: CCCCCC/C=C/CCCC(O)CCO]

(III)

In Formula III the chiral C-3 carbon may be either the (R) enantiomer or the (S) enantiomer.

In another exemplary embodiment, the novel unsaturated, unbranched 1,3-fatty-diol has the has the systematic name: 9-hexadecene-1,3-diol or hexadec-9-ene-1,3-diol. In some exemplary embodiments, the double bond is in (Z) configuration. In other exemplary embodiments, the double bond is in (E) configuration. 9-hexadecene-1,3-diol has the generic structural Formula (IV).

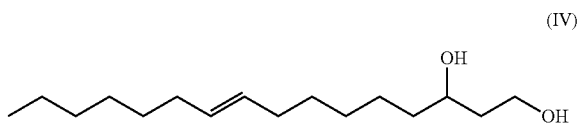 [SMILES: CCCCCC/C=C/CCCCCC(O)CCO]

(IV)

In Formula IV the chiral C-3 carbon may be either the (R) enantiomer or the (S) enantiomer.

1. Physical Properties 1,3-Fatty-Diols

All of the 1,3-fatty-diols disclosed herein comprise two alcohol groups, and a chiral center at the C-3 carbon. Additionally, the unsaturated 1,3-fatty-diols disclosed herein e.g., 5-dodecene-1,3-diol, also comprise a double bond. Thus, the 1,3-fatty-diols disclosed herein are able to undergo a wide array of chemical reactions to form a large variety of molecules. Thus, in addition to the value of any of the 1,3-fatty diols disclosed herein on their own e.g., as a surfactant. In exemplary embodiments, the 1,3-fatty diols disclosed herein e.g., 5-dodecene-1,3-diol, serve as building blocks for an unlimited number of unique and useful derivative molecules.

a. Double Bond

The unsaturated 1,3-fatty-diols disclosed herein e.g., 5-dodecene-1,3-diol, comprise a double bond. Depending on how the 1,3-fatty-diols are produced and/or processed (see herein below), the double bond can be either (Z) or (E). Thus, the unsaturated 1,3-fatty-diols disclosed herein e.g., 5-dodecene-1,3-diol, are able to participate in chemical reactions involving a double bond including e.g., polymerization, alkylation, metathesis, etc. Chemical reactions utilizing the carbon-carbon double bond are known in the art (see e.g., *Practical Synthetic Organic Chemistry: Reactions, Principles, and Techniques*, Stephane Caron ed. (supra)).

Thus, in exemplary embodiments, the carbon-carbon double bond of the unsaturated 1,3-fatty-diols disclosed herein e.g., 5-dodecene-1,3-diol, 9-hexadecene-1,3-diol, etc., participates in addition reactions. Exemplary addition reactions include e.g., halogenation, hydrogenation, hydration, epoxidation, radical polymerization, hydroxylation, etc. Thus, in some exemplary embodiments, the carbon-carbon double bond of an unsaturated 1,3-fatty-diol disclosed herein e.g., 5-dodecene-1,3-diol, 9-hexadecene-1,3-diol, etc., participates in hydrogenation reactions, thus forming the corresponding alkane. In other exemplary embodiments, the carbon-carbon double bond of an unsaturated 1,3-fatty-diol disclosed herein e.g., 5-dodecene-1,3-diol, 9-hexadecene-1,3-diol, etc., participates in hydration reactions to add water across the double bond, thereby yielding a polyol.

In other exemplary embodiments, the carbon-carbon double bond of an unsaturated 1,3-fatty-diol disclosed herein e.g., 5-dodecene-1,3-diol, 9-hexadecene-1,3-diol, etc., participates in polymerization reactions to yield polymers of high industrial value e.g, unique plastics.

b. Hydroxyl Groups

All of the 1,3-fatty-diols disclosed herein e.g., 5-dodecene-1,3-diol, 9-hexadecene-1,3-diol, etc., comprise two hydroxyl functional groups which are available for chemical reactions.

As is generally known in the art, the chemistry of diols is much the same as that of alcohols (see e.g., *Organic Chemistry* ninth edition Francis Carey and Robert Giuliano (2013) supra). Thus, because of the polar nature of the —OH bond the 1,3-fatty-diols disclosed herein e.g., 5-dodecene-1,3-diol, 9-hexadecene-1,3-diol, etc., readily form hydrogen bonds with other 1,3-fatty-diol molecules or other hydrogen-bonding systems (e.g. water). Thus, 1,3-fatty diols generally have relatively high melting and boiling points by comparison with analogous alkanes and relatively high solubility in aqueous media.

The hydroxyl functional groups may participate in the large number of chemical reactions characteristic of hydroxyl groups. Thus, in one exemplary embodiment, the hydroxyl functional groups of the 1,3-fatty-diols disclosed herein e.g., 5-dodecene-1,3-diol, 9-hexadecene-1,3-diol, etc., participate in nucleophilic substitution reactions wherein the hydroxyl acts as a leaving group or where —OH or —O— functions as a nucleophile e.g., substitution with a halide.

In other exemplary embodiments, the hydroxyl functional groups of the 1,3-fatty-diols disclosed herein e.g., 5-dodecene-1,3-diol, 9-hexadecene-1,3-diol, etc., participate in nucleophilic addition reactions wherein the hydroxyl group acts as the nucleophile thereby forming acetals with aldehydes or ketones. Exemplary nucleophilic addition reactions include e.g., glycosylation reactions, which are discussed in more detail herein below.

In still other exemplary embodiments, the hydroxyl functional groups of the 1,3-fatty-diols disclosed herein e.g., 5-dodecene-1,3-diol, 9-hexadecene-1,3-diol, etc., participate in nucleophilic acyl substitution reactions wherein the hydroxyl group acts as the nucleophile to form esters with carboxylic acids and carboxylic acid derivatives e.g., nucleophilic acyl substitution of 5-dodecene-1,3-diol with fatty acids to form e.g., fatty esters.

In still other exemplary embodiments, the hydroxyl functional groups of the 1,3-fatty-diols disclosed herein e.g., 5-dodecene-1,3-diol, 9-hexadecene-1,3-diol, etc., participate in elimination reactions wherein the hydroxyl group is removed as water and a carbon double bond (alkene) is formed.

In still other exemplary embodiments, the hydroxyl functional groups of the 1,3-fatty-diols disclosed herein e.g., 5-dodecene-1,3-diol, 9-hexadecene-1,3-diol, etc., participate in oxidation reactions wherein the hydroxyl group is converted to a carbonyl group (C=O) thus producing a carbonyl compound. In oxidation reactions the resulting carbonyl compound may be an aldehyde, a ketone, or a carboxylic acid depending on the the oxidizing agent used (see e.g., *Organic Chemistry* 9th Edition, Francis Carey and Robert Giuliano (2013) supra).

Thus, the multiple hydroxyl functional groups of the 1,3-fatty-diols disclosed herein e.g., 5-dodecene-1,3-diol, 9-hexadecene-1,3-diol, etc., make a wide variety of reactions possible for the disclosed 1,3-fatty-diols. This in turn offers the possibility of numerous derivatives having unique and useful properties. Some exemplary hydroxyl derivatives of the 1,3-fatty-diols disclosed herein e.g., 5-dodecene-1,3-diol, 9-hexadecene-1,3-diol, etc., are discussed below.

c. Chirality

Chiral molecules, such as e.g., 1,3-fatty-diols e.g., 5-dodecene-1,3-diol, which has a chiral center at the C-3 carbon are building blocks for the synthesis of compounds e.g., pharmaceuticals, nutraceuticals, etc., which are affected by stereochemistry. Since most isomers of chiral drugs exhibit marked differences in biological activities such as e.g., pharmacology, toxicology, pharmacokinetics, biorecognition, metabolism, etc., chirality is an important property to consider e.g., in drug design. Indeed, selecting the appropriate enantiomer can have profound effect on the biological properties of a molecule.

2. Non-Ionic Surfactants

In some exemplary embodiments, the hydroxyl functional groups of the 1,3-fatty-diols disclosed herein e.g., 5-dodecene-1,3-diol, 9-hexadecene-1,3-diol, etc., are used to prepare non-ionic surfactants.

i. Glycosylated Derivatives

In exemplary embodiments, the hydroxyl moieties of the 1,3-fatty-diols disclosed herein e.g., 5-dodecene-1,3-diol, are available for reaction with sugars to provide alkyl polyglycosides. Alkyl poyglycosides are a class of non-ionic surfactants derived from sugars and fatty alcohols and are well known in the art (see e.g., *Alkyl Polyglycosides: Technology, Properties, Applications*, Karlheinz Hill; Wolfgang von Rybinski; Gerhard Stoll, eds. Wiley (2008); *Novel Surfactants: Preparation Applications And Biodegradability*, Surfactant Science Series. Volume 114 Second Edition, Krister Holmberg ed. Marcel Dekker: New York and Basel, Switzerland. 2003). Thus, in exemplary embodiments, a 1,3-fatty-diol as disclosed herein e.g., 5-dodecene-1,3-diol, is reacted with e.g., xylose, galactose, mannose, glucose, etc. to form alkyl polyglycosides with new and useful properties.

When derived from glucose, alkyl polyglycosides are referred to as alkyl polyglucosides. Thus, in exemplary embodiments, a 1,3-fatty-diol as disclosed herein e.g., 5-dodecene-1,3-diol, 9-hexadecene-1,3-diol, etc., is reacted with glucose to form alkyl polyglucosides. Alkyl polyglucosides are known in the art (see e.g., *Nonionic Surfactants: Alkyl Polyglucosides*. Surfactant Science Series. Volume 91 Dieter Balzer and Harald Lüders, eds. Marcel Dekker: New York and Basel, Switzerland. 2000; Rather and Mishra: β-*Glycosidases: An alternative enzyme based method for synthesis of alkyl-glycosides*. Sustainable Chemical Processes 2013 1:7).

Alkyl polyglycosides may be prepared by any method known in the art. Exemplary methods suitable for the preparation of glycosylated molecules as disclosed herein include e.g., U.S. Pat. Nos. 5,449,763, 3,547,828, 3,839,318; Böge, K., Tietze, L. "Synthesis of alkyl polyglycosides: Effect of catalyst-type on reaction rate and product composition" *Eur. J. Lipid Sci. Tech.* (1998) 100, 38-41; Rybinski, W., Hill, K. "Alkyl Polyglycosides—Properties and Applications of a new Class of Surfactants" *Angew. Chem. Int. Ed.* (1998) 37(10), 1328-1345; "Handbook of Chemical Glycosylation: Advances in Stereoselectivity and Therapeutic Relevance" Ed. A. V. Demchenko, John Wiley & Sons, Apr. 9, 2008; Luley-Goedl, C. et al. *Carbohydrate Research* (2010) 345, 1736-1740; Rather, M. Y., Mishra, S. (2013) supra; Ojha, S. et al. "Synthesis of hexyl α-glucoside and α-polyglucosdies by a novel *Microbacterium* isolate" *Appl. Microbiol. Biotechnol.* (2013) 97, 5293-5301; Wooten, J. "Glycosylation of Amino Acids and Efficient Synthesis of Glycosphingolipids" Thesis, Georgia State University, 2015).

Thus, in exemplary embodiments, the present disclosure provides an alkylpolyglycoside having a general formula according to Formula V and/or Formula VI.

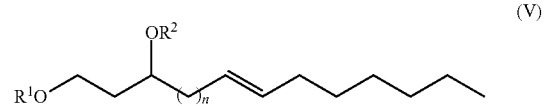

(V)

In Formula (V), n is an integer selected from 0, 1, 2, 3, 4, 5, 6, 7, 8, 9, 10, 11, 12, 13 and 14, the double bond may be in either the (Z) or the (E) configuration and the C-3 carbon may be either an (R) or an (S) enantiomer.

Furthermore, in Formula (V), $R^1$ and $R^2$ are each independently H, a monosaccharide bound at an anomeric carbon of the monosaccharide, a disaccharide bound at an anomeric carbon of the disaccharide, a trisaccharide bound at an anomeric carbon, or a polysaccharide bound at an anomeric carbon. In exemplary embodiments, $R^1$ and $R^2$ cannot both be H. In other exemplary embodiments, neither $R^1$ nor $R^2$ are H.

In exemplary embodiments, the monosaccharide is selected from pentose sugars and hexose sugars. In some exemplary embodiments, the hexose sugar selected from allose, altrose, glucose, mannose, gulose, iodose, galactose or talose. In other exemplary embodiments, the disaccharide, the trisaccharide, and/or the polysaccharide comprise sugars selected from pentose sugars, hexose sugars or a mixture of any two or more thereof. In some exemplary embodiments, the hexose sugar selected from allose, altrose, glucose, mannose, gulose, iodose, galactose, talose, or a mixture of any two or more thereof. In some exemplary embodiments, $R^1$ and $R^2$ are different monosaccharides. In other exemplary embodiments, $R^1$ and $R^2$ are the same monosaccharide.

In exemplary embodiments, the monosaccharide, the disaccharide, the trisaccharide, and/or the polysaccharide comprise a hexose sugar selected from allose, altrose, glucose, mannose, gulose, iodose, galactose, talose, or a mixture of any two or more thereof. In other exemplary embodiments, the monosaccharide, disaccharide, trisaccharide, or polysaccharide comprises a sugar selected from furanose sugars, pyranose sugars, or a mixture of any two or more thereof.

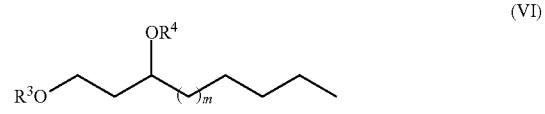

(VI)

In Formula (VI), m is an integer selected from 1, 2, 3, 4, 5, 6, 7, 8, 9, 10, 11, 12, 13, 14, 15, 16, 17 and 18 and the C-3 carbon may be either an (R) or an (S) enantiomer.

Furthermore, in Formula (VI), $R^3$ and $R^4$ are each independently H, a monosaccharide bound at an anomeric carbon of the monosaccharide, a disaccharide bound at an anomeric carbon of the disaccharide, a trisaccharide bound at an anomeric carbon, or a polysaccharide bound at an anomeric carbon. In exemplary embodiments, $R^3$ and $R^4$ cannot both be H. In other exemplary embodiments neither $R^3$ nor $R^4$ are H.

In exemplary embodiments, the monosaccharide is selected from pentose sugars and hexose sugars. In other exemplary embodiments, the disaccharide, the trisaccharide, and/or the polysaccharide comprise sugars selected from pentose sugars, hexose sugars or a mixture of any two or more thereof. In some exemplary embodiments, $R^3$ and $R^4$ are different monosaccharides. In other exemplary embodiments, $R^3$ and $R^4$ are the same monosaccharide.

In exemplary embodiments, the monosaccharide, the disaccharide, the trisaccharide, and/or the polysaccharide comprise a sugar selected from allose, altrose, glucose, mannose, gulose, iodose, galactose, talose, or a mixture of any two or more thereof. In still other exemplary embodiments, the monosaccharide, disaccharide, trisaccharide, or polysaccharide comprises a sugar selected from furanose sugars, pyranose sugars, or a mixture of any two or more thereof.

The term "anomeric carbon" as applied to any compound of the present technology herein is well understood by a person of skill in the art, where an example of attachment at the anomeric carbon of the saccharide is illustrated by the glucosylated variant below:

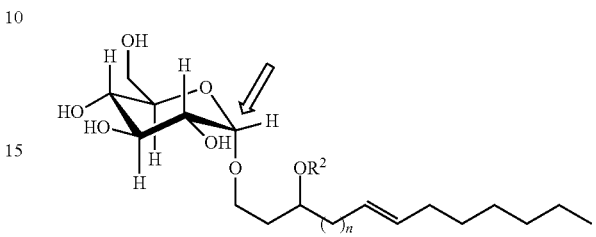

The anomeric carbon of the saccharide (here, a monosaccharide) is indicated by the open arrow. Similarly, a glucose disaccharide includes those illustrated in the following two Schemes:

Scheme 1: An α(1→4) Disaccharide (α-Maltose) with an α-Glycosidic Bond to the Non-Sugar Chain

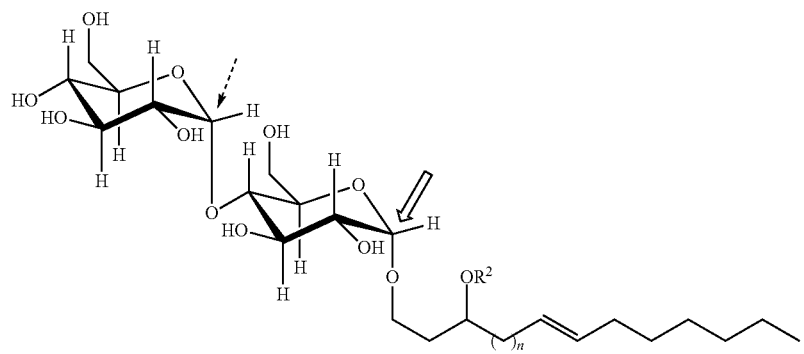

Scheme 2: An α(1→6) Disaccharide (α-Isomaltose) with an α-Glycosidic Bond to the Non-Sugar Chain

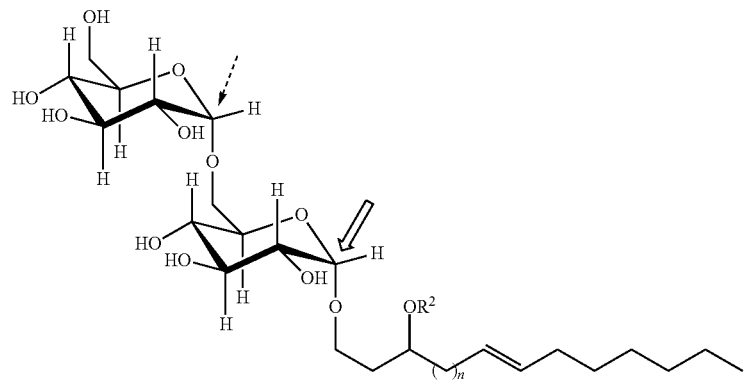

As illustrated by Schemes 1 and 2, when e.g., indicating $R^1$ is "bound at an anomeric carbon" of the disaccharide maltose or isomaltose, this is to be understood as referring to the anomeric carbon of the free disaccharide bearing a free hydroxyl group that is susceptible to such bond formation with, e.g., a compound of Formulas IA, IB, II, III, IV, as indicated by the open arrow above, not the anomeric carbon(s) involved in the linkage (hereinafter, a "glycosidic linkage") between the saccharides for di-, tri-, and polysaccharides as indicated by the dashed arrow. This applies to the meaning of "bound at an anomeric carbon" in reference to trisaccharides and polysaccharides. Thus, in any embodiment herein, when $R^1$, $R^2$, $R^3$, and/or $R^4$ is a monosaccharide, disaccharide, trisaccharide, and/or polysaccharide, $R^1$, $R^2$, $R^3$, and/or $R^4$ may be bound via a α-glycosidic bond or a β-glycosidic bond. Moreover, the disaccharide, trisaccharide, and/or polysaccharide may be saccharides that include an α-glycosidic linkage, a β-glycosidic linkage, or (for trisaccharides and/or polysaccharides) mixtures thereof.

In exemplary embodiments, the monosaccharide is selected from pentose sugars and hexose sugars. In other exemplary embodiments, the disaccharide, the trisaccharide, and/or the polysaccharide comprise sugars selected from pentose sugars, hexose sugars or a mixture thereof. In some exemplary embodiments, $R^3$ and $R^4$ are different monosaccharides. In other exemplary embodiments, $R^3$ and $R^4$ are the same monosaccharide.

In exemplary embodiments, the monosaccharide, the disaccharide, the trisaccharide, and/or the polysaccharide comprise a sugar selected from allose, altrose, glucose, mannose, gulose, iodose, galactose, talose, or a mixture of any two or more thereof. In still other exemplary embodiments, the monosaccharide, disaccharide, trisaccharide, or polysaccharide comprises a sugar selected from furanose sugars, pyranose sugars, or a mixture thereof.

Thus, in any embodiment herein, the monosaccharide, disaccharide, trisaccharide, or polysaccharide may comprise pentose sugars, hexose sugars, or (when $R^1$ and $R^2$ or $R^3$ and $R^4$ are different monosaccharides and/or for any one or more disaccharide, trisaccharide, or polysaccharide) a mixture of any two or more thereof. The monosaccharide, disaccharide, trisaccharide, or polysaccharide of any embodiment herein may comprise allose, altrose, glucose, mannose, gulose, iodose, galactose, talose, or (when $R^1$ and $R^2$ or $R^3$ and $R^4$ are different monosaccharides and/or for any one or more disaccharide, trisaccharide, or polysaccharide) a mixture of any two or more thereof. Moreover, in any embodiment herein, the monosaccharide, disaccharide, trisaccharide, or polysaccharide may comprise furanose sugards, pyranose sugars, or (when $R^1$ and $R^2$ or $R^3$ and $R^4$ are different monosaccharides and/or for any one or more disaccharide, trisaccharide, or polysaccharide) a mixture of any two or more thereof. In any embodiment herein, $R^1$, $R^2$, $R^3$, and $R^4$ may each independently be H or

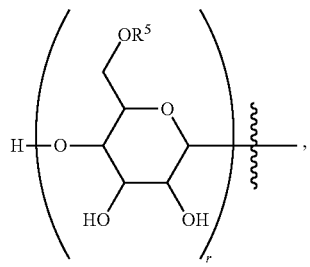

where $R^5$ is independently at each occurrence H or

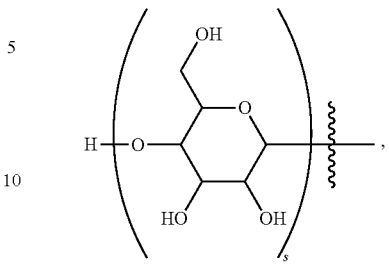

r is an integer from 1, 2, 3, 4, 5, 6, 7, 8, 9, or 10, and s is 1, 2, 3, 4, 5, 6, 7, 8, 9, or 10. In any embodiment herein, $R^1$, $R^2$, $R^3$, $R^4$, and $R^5$ may each independently include allose, altrose, glucose, mannose, gulose, iodose, galactose, talose, or (when any two or more of $R^1$, $R^2$, $R^3$, $R^4$, and $R^5$ are different monosaccharides and/or for any one or more disaccharide, trisaccharide, or polysaccharide) a mixture of any two or more thereof. in any embodiment herein, when $R^1$, $R^2$, $R^3$, $R^4$, and/or $R^5$ is a monosaccharide, disaccharide, trisaccharide, and/or polysaccharide as indicated above, $R^1$, $R^2$, $R^3$, $R^4$, and/or $R^5$ may be bound via a α-glycosidic bond or a β-glycosidic bond. Moreover, the disaccharide, trisaccharide, and/or polysaccharide of $R^1$, $R^2$, $R^3$, $R^4$, and/or $R^5$ indicated in the structural formulas above may be saccharides that include α-glycosidic linkages, β-glycosidic linkages, or (for trisaccharides and/or polysaccharides) mixtures of any two or more thereof.

a. Compositions Comprising Alkylpolyglucosides

Alkyl polyglycosides are particularly useful molecules which may be advantageously incorporated into numerous industrial agents and processes. Indeed, alkyl polyglycosides find use e.g., as emulsifiers, emollients, and thickeners in cosmetics and foods, in agricultural formulations e.g., in pesticide formulations to deliver active ingredients to a target e.g., waxy surface of leaves, as industrial solvents, in the oil and gas industries to enhance oil recovery, as plasticizers, as surfactants and detergents and in the production of surfactants and detergents, etc.

Alkyl polyglycoside surfactants are particularly valued in that they enjoy advantages over other surfactants with regard dermatological properties, compatibility with standard products, as well as a favorable environmental profile. Thus, they are widely used in a variety of household and industrial applications e.g., in pharmaceuticals, for solubilization of hydrophobic drugs in aqueous media, as components of emulsion or surfactant self-assembly vehicles for oral and transdermal drug delivery, as plasticizers in semisolid delivery systems, as agents to improve drug absorption and penetration, etc. Thus, in exemplary embodiments, alkyl polyglycosides are incorporated in personal care products as a bio-based ingredient that is e.g., less irritating to the skin than other surfactants and solubilizing agents with reduced toxicological profiles.

Therefore, in exemplary embodiments, a personal care composition is provided that comprises a compound as disclosed herein and a cosmetically acceptable carrier.

Personal care products are known in the art see e.g., *Surfactants in Personal Care Products and Decorative Cosmetics*, Third Edition, Linda D. Rhein, Mitchell Schlossman, Anthony O'Lenick, P. Somasundaran, eds. CRC Press (2006). In one exemplary embodiment, the personal care product is a skin care composition. Skin care compositions are known in the art see e.g., *Cosmetic Formulation of Skin Care Products*, Zoe Diana Draelos, Lauren A. Thaman, eds. CRC Press (2005).

In exemplary embodiments, the cosmetically acceptable carrier in the personal care composition is selected from the group consisting of water, emollients, fatty acids, fatty alcohols, thickeners, and combinations thereof.

In one exemplary embodiment, the personal care composition comprises water at a concentration that is between about 40 weight percent (wt %) to about 96 wt %.

In another exemplary embodiment, personal care composition comprises an emollient selected from the group consisting of silicone oils, natural or synthetic esters, hydrocarbons, alcohols, fatty acids, and combinations thereof. In some exemplary embodiments, the emollients are present in a concentration that is between about 0.1 wt % to about 60 wt % of the personal care composition. In other exemplary embodiments the emollients are present in a concentration that is between about 30 wt % to about 50 wt %.

In another exemplary embodiment, personal care composition comprises silicone oils. Silicone oils may be divided into the volatile and nonvolatile variety. The term "volatile" as used herein refers to those materials which have a measurable vapor pressure at ambient temperature. Volatile silicone oils are preferably chosen from cyclic polydimethylsiloxanes (cyclomethicones) or linear polydimethylsiloxanes containing from 3, 4, 5, 6, 7 8, or 9 silicon atoms, preferably from 5 to 6 silicon atoms. Nonvolatile silicone oils include polyalkyl siloxanes, polyalkylaryl siloxanes, and polyether siloxane copolymers. Nonvolatile polyalkyl siloxanes useful herein include, for example, polydimethyl siloxanes with viscosities from about $5\times10-6$ m$^2$/s to about 0.1 m$^2$/s at 25° C., preferably from about $1\times10-5$ m$^2$/s to about $4\times10-4$ m$^2$/s at 25° C. Other classes of nonvolatile silicones are emulsifying and non-emulsifying silicone elastomers, such as DimethiconeNinyl Dimethicone Crosspolymer (available as Dow Corning 9040, General Electric SFE 839, and Shin-Etsu KSG-18). Silicone waxes, such as Silwax WS-L (Dimethicone Copolyol Laurate), may also be included in any one of the embodiments of the personal care compositions described herein.

In another exemplary embodiment, personal care composition comprises ester emollients. In another exemplary embodiment, the ester emollient is an alkyl ester of saturated fatty acids having 10 to 24 carbon atoms. In exemplary embodiments, the alklester is a member selected from the group consisting of behenyl neopentanoate, isononyl isononanoate, isopropyl myristate and octyl stearate.

In another exemplary embodiment, personal care composition comprises ether-esters (such as fatty acid esters) of ethoxylated saturated fatty alcohols.

In another exemplary embodiment, the personal care composition comprises polyhydric alcohol esters, such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol polyfatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. In another exemplary embodiment, the polyhydric alcohol ester is selected from the group consisting of pentaerythritol, trimethylolpropane and neopentyl glycol esters of C1-C30 alcohols.

In another exemplary embodiment, personal care composition comprises waxesters such as beeswax, spermaceti wax and tribehenin wax.

In another exemplary embodiment, personal care composition comprises sugar esters of fatty acids, such as e.g., sucrose polybehenate and sucrose polycottonseedate.

In some exemplary embodiments, the personal care composition comprises natural ester emollients. Natural ester emollients principally are based upon mono-, di- and triglycerides. Representative examples include sunflower seed oil, coconut oil, cottonseed oil, borage oil, borage seed oil, primrose oil, castor and hydrogenated castor oils, rice bran oil, soybean oil, olive oil, safflower oil, shea butter, jojoba oil and combinations of any two or more thereof. Animal-derived emollients include, for example, lanolin oil and lanolin derivatives. In exemplary embodiments, the amount of the natural ester is present in a concentration that is in a range that is between about 0.1 wt % to about 20 wt % of the personal care composition.

In some exemplary embodiments, the personal care composition comprises hydrocarbons. Hydrocarbons which are suitable cosmetically acceptable carriers include e.g., petrolatum, mineral oil, C8-C30 n-alkanes, C8-C30 n-alkenes, C11-C13 isoparaffins, polybutenes, and especially isohexadecane (available commercially as Permethyl 101A from Presperse Inc.).

In some exemplary embodiments, the personal care composition comprises fatty acids. In general, fatty acids having from 6 to 30 carbon atoms are provided as cosmetically acceptable carriers. In some exemplary embodiments, fatty acids having 10 to 30 carbon atoms are provided as cosmetically acceptable carriers. In other exemplary embodiments, fatty acids having 8 to 24 carbon atoms are provided as cosmetically acceptable carriers. In still other exemplary embodiments, fatty acids having 6 to 24 carbon atoms are provided as cosmetically acceptable carriers.

Some exemplary 1-30 carbon fatty acids include pelargonic, lauric, myristic, palmitic, stearic, isostearic, oleic, linoleic, linolenic, hydroxystearic and behenic acids, and mixtures of any two or more thereof. Fatty alcohols having from 10 to 30 carbon atoms are another useful category of cosmetically acceptable carrier. Illustrative of this category are stearyl alcohol, lauryl alcohol, myristyl alcohol, oleyl alcohol, cetyl alcohol, and mixtures of any two or more thereof.

In some exemplary embodiments, the personal care composition comprises thickeners. Exemplary thickeners include crosslinked acrylates (e.g., Carbopol 982®), hydrophobically-modified acrylates (e.g., Carbopol 1382®), polyacrylamides (e.g., Sepigel 305®), acryloylmethylpropane sulfonic acid/salt polymers and copolymers (e.g., Aristoflex HMB® and AVC®), cellulosic derivatives, natural gums, and combinations of any two or more thereof. Among useful cellulosic derivatives are sodium carboxymethylcellulose, hydroxypropyl methocellulose, hydroxypropyl cellulose, hydroxyethyl cellulose, ethyl cellulose, hydroxymethyl cellulose, and combinations of any two or more thereof. Natural gums include, but are not limited to, guar, xanthan, sclerotium, carrageenan, pectin, and combinations of any two or more thereof. Inorganics may also be utilized as thickeners, particularly clays such as bentonites and hectorites, fumed silicas, talc, calcium carbonate and silicates such as magnesium aluminum silicate (Veegum®), as well as combinations of any two or more of these organics. Combinations of any two or more thickeners are also useful in the personal care compositions of the present technology. Amounts of the thickener may range from about 0.0001 wt % to about 10 wt %, preferably about 0.001 wt % to about 1 wt %, and optimally may be from about 0.01 wt % to about 0.5 wt % of the personal care composition.

In some exemplary embodiments, the personal care composition comprises humectants. In exemplary embodiments, humectants of the polyhydric alcohol-type are employed as cosmetically acceptable carriers. Exemplary polyhydric alcohols include, e.g., glycerol, polyalkylene glycols (more preferably alkylene polyols and their derivatives, including propylene glycol, dipropylene glycol, polypropylene glycol, polyethylene glycol and derivatives thereof), sorbitol, hydroxypropyl sorbitol, hexylene glycol, 1,3-butylene glycol, isoprene glycol, 1,2,6-hexanetriol, ethoxylated glycerol, propoxylated glycerol, and mixtures thereof. In exemplary embodiments, the amount of humectant is present in a concentration that is between about 0.5 wt % to about 50 wt % of the personal care composition. In exemplary embodiments, the amount of humectant present in the personal care composition is between about 0.5 wt % to about 50 wt %. In some exemplary embodiments, when a humectant is included, it is included in an amount of that is between about 1 wt % and 15 wt % of the personal care composition.

In some exemplary embodiments, skin moisturizers are included as a cosmetically acceptable carrier. Thus, in exemplary embodiments, hyaluronic acid and/or its precursor N-acetyl glucosamine are included as a cosmetically acceptable carrier. In some exemplary embodiments, N-acetyl glucosamine is derived from shark cartilage or shitake mushrooms and are available commercially from Maypro Industries, Inc (New York). In other exemplary embodiments, the skin moisturizers are included as a cosmetically acceptable carrier are hydroxypropyl tri(C1-C3 alkyl)ammonium salts. In some exemplary embodiments hydroxypropyl tri(C1-C3 alkyl)ammonium salts are obtained from synthetic procedures, e.g., from hydrolysis of chlorohydroxypropyl tri(C1-C3 alkyl)ammonium salts. In still other exemplary embodiments, moisturizing agents, especially when used in conjunction with the aforementioned ammonium salts, include e.g., substituted ureas such as hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra (hydroxyethyl) urea; tetra(hydroxypropyl urea; N-methyl-N'-hydroxyethyl urea; N-ethyl-N'-hydroxyethyl urea; N-hydroxypropyl-N'-hydroxyethyl urea, N,N'-dimethyl-N-hydroxyethyl urea.

In another exemplary embodiment, personal care composition comprises has a pH of between about 4 to about 8. In some exemplary embodiments the pH of the personal care composition is about 4, about 4.5, about 5, about 5.5, about 6, about 6.5, about 7, about 7.5, about 8, or any range including and between any two of these values. In one exemplary embodiment, the pH of the personal care composition is between about 5 to about 7. In other exemplary embodiments, the pH of the personal care composition is between about 5 to about 6.

In another exemplary embodiment, personal care composition comprises inorganic sunscreen. In one exemplary embodiment, the amount of inorganic sunscreen is present at a concentration that is between about 0.1 wt % to about 10 wt % of the personal care composition. Inorganic sunscreens are well known in the art and include, but are not limited to, zinc oxide, iron oxide, silica (e.g., fumed silica), and titanium dioxide.

In some exemplary embodiments, personal care composition comprises a cosmetic benefit ingredient. Exemplary cosmetic benefit ingredients include, but are not limited to, skin lightening ingredients, retinoids, herbal extracts, anti-fungal agents, resveratrol, alpha-lipoic acid, ellagic acid, kinetin, retinoxytrimethylsilane, ceramides, pseudoceramides, colorants, opacifiers, abrasives, and combinations thereof.

ii. Ethoxylated Derivatives

In exemplary embodiments, the hydroxyl moieties of 5-dodecene-1,3-diol are available for ethoxylation to prepare novel alcohol ethoxylates, ethoxysulfates, propoxylates and butoxylates, fatty alcohol polyglycolethers, etc. Alcohol ethoxylates are known in the art (see e.g., U.S. Pat. No. 4,223,163; Surfactants. In Elvers, Barbara, et al. Ullmann's Encyclopedia of Industrial Chemistry. Weinheim, GER: Wiley-VCH).

Fatty alcohol ethoxylates were the first nonionic surfactants to be manufactured in technical scale. They are used widely in cosmetic and other commercial products such as e.g., detergents, cleaners, etc.

3. Polyurethanes

In some exemplary embodiments, the hydroxyl functional groups of 5-dodecene-1,3-diol are used to prepare polyurethanes.

The double bond of the 5-dodecene-1,3-diol serves as a site for epoxidation, as shown e.g. in Formula VII

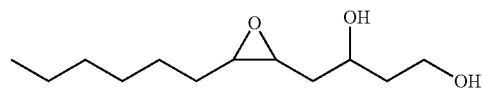

(VII)

As is known in the art, standard epoxidation chemistry involves heat between 30° C.-80° C. using hydrogen peroxide and a catalyst in the class of Jacobsen catalysts or a TS-1 zeolite catalyst.

In exemplary embodiments, the alcohol groups of 5-dodecene-1,3-diol are prevented from reacting themselves at the epoxy ring by protecting group chemistry such as acetyl groups, as known in the art (see e.g., *Practical Synthetic Organic Chemistry*, Stephane Caron ed. (2011) supra; *Organic Chemistry*, 9$^{th}$ Edition, Carey and Giuliano (2013) supra) and as shown e.g., in Formula VIII

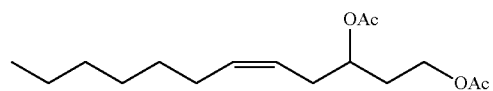

(VIII)

In exemplary embodiments, using methods known in the art, water is used to ring-open the epoxy ring on the derivatized 5-dodecene-1,3-diol thereby leading to a tetraol, as shown e.g., in Formula IX.

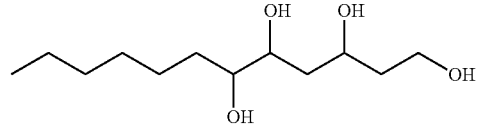

(IX)

In other exemplary embodiments, using methods known in the art, a hydrogen reactant is used to open the epoxy ring thereby leading to a triol, as shown e.g., in Formula X

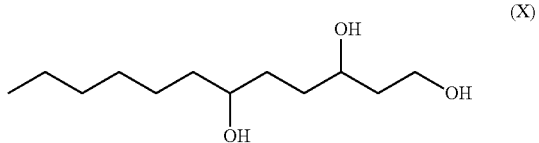
(X)

In exemplary embodiments, the use of a selective ring-opening with hydrogen to the dodecane-1,3,6-triol is preferred. Epoxide chemistry is vast and widely used, and other diols, alcohols, and functionalized moieties may be reacted at this site (Y. Li et al., *Bio-based Polyols and Polyurethanes*, Springer Briefs in Green Chemistry for Sustainability, DOI 10.1007/978-3-319-21539-6_2).

In other exemplary embodiments, using a one step "single pot" reaction as known in the art (see e.g., Monteavaro L L, et al. J Am. Oil Chem. Soc. 82:365-371, 2005) alcohol groups on the 5-dodecene-1,3-diol are used to ring-open at the epoxy, leading to a structure such as that shown in e.g., Formula XI.

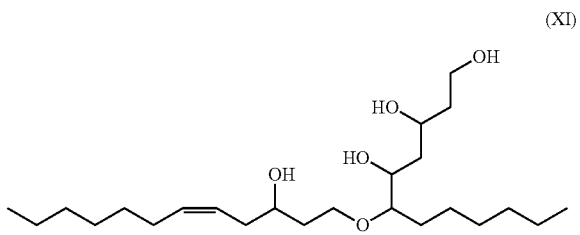 [SMILES: CCCCCC/C=C\CC(O)CCOC(CCCCCC)C(O)CC(O)CCO]
(XI)

Using alcohol groups on the 5-dodecene-1,3-diol to ring-open at the epoxy provides branched polyols that have higher viscosity than the original 5-dodecene-1,3-diol. High viscosity polyols are useful in applications such as e.g., oil exploration and recovery, paints and coatings, and personal care.

In other exemplary embodiments, reacting the dodecane-1,3,6-triol of Formula X with the epoxide of Formula VII provides branched polyols of Formula XII.

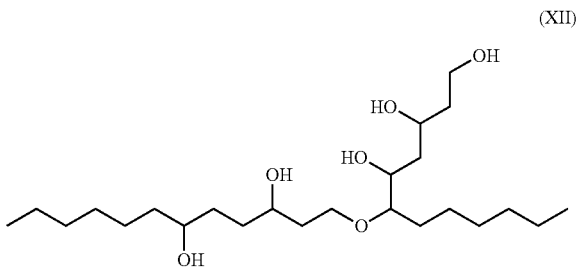 [SMILES: CCCCCCC(O)CCC(O)CCOC(CCCCCC)C(O)CC(O)CCO]
(XII)

In exemplary embodiments, polyols produced from 5-dodecene-1,3-diol are further derivatized, for example by co-polymerizing with ethylene oxide, thereby providing polyether polyols. The resulting polyether polyols may be used as-is in various applications, e.g., as building blocks of polyurethanes.

In exemplary embodiments, a 5-dodecene-1,3-diol, associated triol or tetraol as disclosed herein, or associated branched or other polyols produced using 5-dodecene-1,3-diol as disclosed herein, may proceed in standard chemistries with isocyanate compounds to form polyurethanes. These reactions may be promoted by ultraviolet light or by catalysts such as e.g., dibutyltin dilaurate or bismuth octanoate by methods known in the art (see e.g., Y. Li et al., *Bio-based Polyols and Polyurethanes*, Springer Briefs in Green Chemistry for Sustainability, DOI 10.1007/978-3-319-21539-6_2). Many different isocyanates, ranging from linear to aromatic, may be used; and techniques for preparing the polymer may or may not go through a pre-polymer phase, for instance prepping the diol, triol, or polyols with isocyanate groups (see e.g., U.S. Pat. No. 4,532,316).

In exemplary embodiments, carbamates are used as intermediates for the synthesis of isocyanates as well as for direct conversions with diols to prepare non-isocyanate polyurethanes (NIPUs; see e.g., Maisonneuve, L. et al. (2015) Chem. Rev. 115:12407-12439). Non-isocyanate polyurethanes are particularly useful to the world because they allow the performance and properties of polyurethanes, used in such diverse applications from construction materials to medical devices, to be produced without the use of carcinogenic isocyanates. This enables safer working conditions for producers, commercial users, and even everyday consumers who may be exposed when using polyurethane products such as coatings and adhesives. Accordingly, use of 5-dodecene-1,3-diol in the preparation of NIPUs allows avenues to new carbonate structures with improved reactivity over 1,2-diols (1,3-diol to 6-membered ring versus 1,2-diol to 5-membered ring), combined with cross-linking or rearrangement flexibility afforded by the double bond, to provide new non-isocyanate polyurethane products.

To prepare NIPUs, 5-dodecene-1,3-diol may be used as a diol, or converted to a polyol as discussed above, and used in reactions with a wide variety of carbamates (see e.g., Rokocki, G, et al. Polym. Adv. Technol. 26, 707-761, 2015). The 1,3-diol arrangement in the 5-dodecene-1,3-diol has the advantage over 1,2-diols in that there is less steric hindrance by the alcohol reaction centers.

The hydroxyl moieties of 5-dodecene-1,3-diol are available for reaction with dimethyl carbonate or carbon dioxide to prepare a 6-membered cyclic carbonate ring that is subsequently reacted with a primary amine to provide novel "non-isocyanate" polyurethanes (NIPUs). The carbonate is useful for further reaction to NIPUs if it is double-ended, that is, if it is first reacted with itself in a cross-linked or a metathesis reaction to give two ends for which to continue a polymer chain; this may be done before or after the carbonate structure has been formed. Thus, the branched polyol in Formula XII may also be converted to a 2-carbonate polymer building block, e.g., Formula XIII.

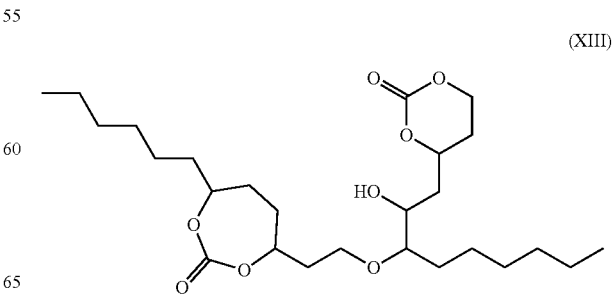
(XIII)

Exemplary catalysts that may be used to create carbonate derivatives from 5-dodecene-1,3-diol, or a tetraol produced from 5-dodecene-1,3-diol, include e.g., 1,5,7-triazabicyclo[4.4.0]dec-5-ene with dimethyl carbonate (Mutlu et al, *Green Chem.*, 2012); various imidazolium or thiazolium carbene catalysts in the presence of cesium carbonate, dibromomethane, and $CO_2$ at atmospheric pressure (Bobbink et al, *Chem. Commun.*, 2016); and $CeO_2$ with 2-cyanopyridine in the presence of $CO_2$ (Honda et al, *ACS Catal.*, 2014).

A 6-membered cyclic carbonate from a 1,3-diol moiety such as those produced from 5-dodecene-1,3-diol has a 30× reactivity versus a 5-membered cyclic carbonate from a 1,2-diol moiety and is thus preferable in use (Maisonneuve et al, *Chem. Rev.*, 2015, supra).

In exemplary embodiments, Self-metathesis to form "double-ended" structures employs a metathesis catalyst known in the art, for example a first or second generation Grubbs catalyst, one specific example being bis(tricyclohexylphosphine)dichloro ruthenium (II) benzylidene, [(PCy3)2Cl2]Ru=CHPh (see e.g., International Application No. PCT/US95/09655).

A metathesis reaction is driven under vacuum to pull the internal olefin side product away. In some exemplary embodiments, the metathesis reaction is performed before the carbonate is formed, that is diol to tetraol, see Formula XIV. Formula XIV as a polyol has applications as discussed above.

In some exemplary embodiments, 5-dodecene-1,3-diol, or related 6-membered cyclic carbonate, is first reacted in an ethylene metathesis to form the terminal alkene counterparts, shown in below.

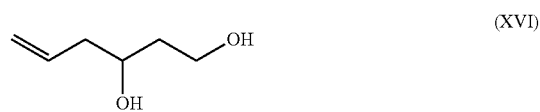

(XVI)

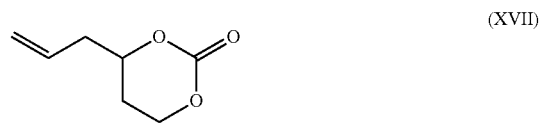

(XVII)

Subsequently a self-metathesis of Formula XVI and Formula XVII respectively, provides double-ended compounds of Formulas XIV and XV respectively.

Further reactions of Formula XV may be performed across the double bond to add rigidity, explore increase in glass transition temperature (Tg) of subsequent polymers, or add pendant groups. In an exemplary embodiment, reacting Formula XV in a standard Diels-Alder reaction with butadiene and a Lewis acid provides Formula XVIII.

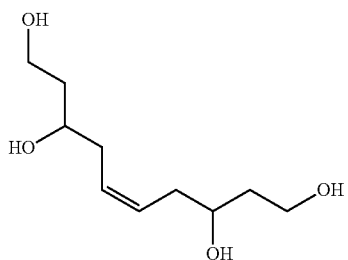

(XIV)

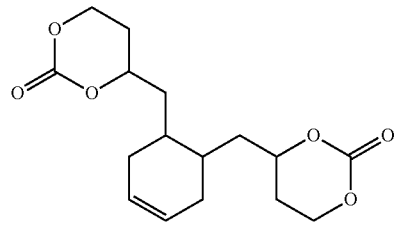

(XVIII)

Alternatively, the carbonate may be produced from the diol first, then self-metathesized to the double-ended carbonate. That is, 6-membered cyclic carbonate molecule produced from the 5-dodecene-1,3-diol is then self-metathesized to a molecule with two 6-membered cyclic carbonates, thus providing a molecule of see Formula XV. The metathesis reaction may lead to a mixture of cis and trans double bonds.

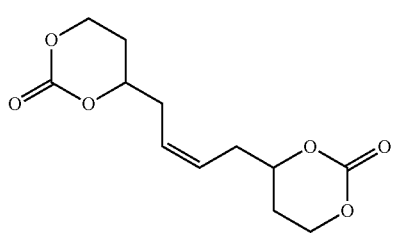

(XV)

4. Polyesters

As noted supra, the 1,3-diol structure has less steric hindrance than, for instance, a 1,2-diol of analogous chain length, aiding in polymer formation.

Chemistries for forming polyesters have been studied for over 100 years, and are well known in the art. Exemplary chemistries include, but are not limited to, reactions catalyzed by heat and acid; lipase enzyme catalyzed polycondensation; the use of scandium triflates as catalysts, etc (see e.g., Díaz, A. et al., *Macromolecules* 2005, 38, 1048-1050).

In exemplary embodiments, 5-dodecene-1,3-diol is reacted with diacids such as e.g., adipic acid to form "bushy" polyesters, such as e.g., the molecule shown below as Formula XIX, where n is an integer from 1-1000.

(XIX)

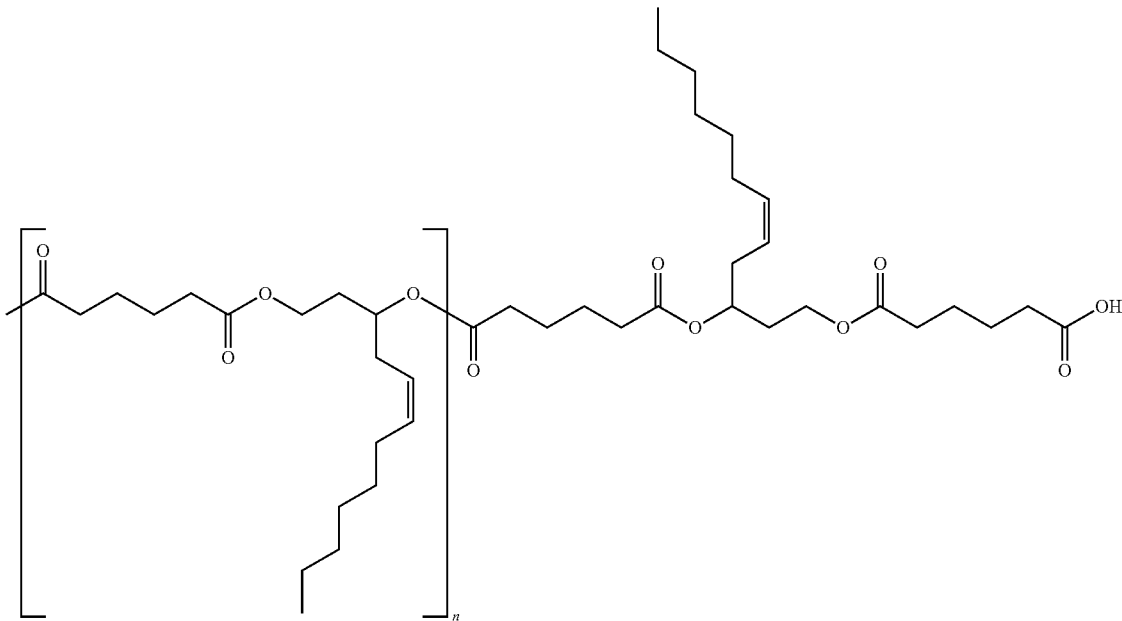

The "bushy" character of the polyester structure, compared to, for instance, a polyester produced with alpha-omega diols (1,2-diols), will have less crystallinity and improved performance in micelle formation in surfactants as well as lending hydrophobicity in other polymer applications.

The structure of the 5-dodecene-1,3-diol functions to influence crystallinity e.g., promoting less crystallinity, and Glass Transition Temperature (Tg); polymer phase interactions; extruding properties; and solubility and surface interactions with water, solvents, and complex formulations. Thus, in exemplary embodiments, 5-dodecene-1,3-diol is used as an additive to increase hydrophobicity and give a plasticizer effect. Thus, in exemplary embodiments, 5-dodecene-1,3-diol is used in a concentration of between about 0.001% to about 45% of diol or polyols species, to impact the structure of known polyesters. Thus, in exemplary embodiments, 5-dodecene-1,3-diol is incorporated into polybutyrate, a copolyester of adipic acid, 1,4-butanediol and dimethyl terephthalate, in lower percentage than the main monomers, to provide a molecule such as e.g., that shown below as Formula XX, where in and n are each independently integers from 1-1000.

(XX)

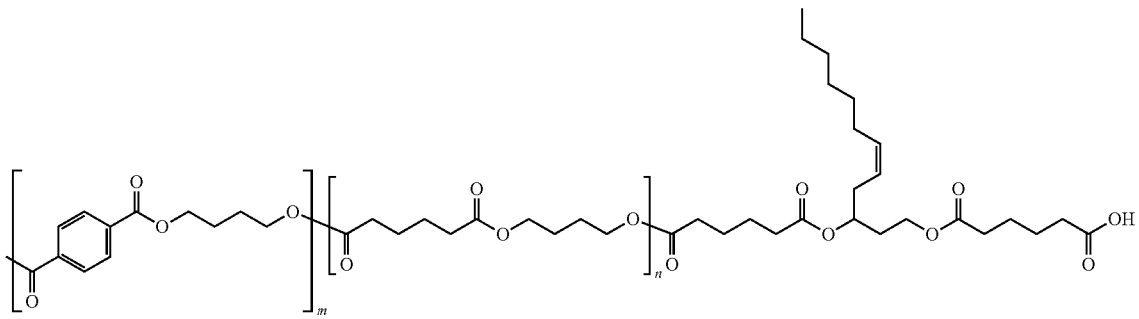

II. Preparation of (Z)-5-Dodecene-1,3-Diol a. General Pathways for Biological Synthesis 5-dodecene-1,3-diol can be made by any method known in the art. As discussed supra, unsaturated fatty alcohols are difficult to produce from petroleum. Rather, unsaturated fatty alcohols are typically produced from processing of non-petroleum sources such as fats and oils of plant and animal origin (see e.g., E. F. Hill, et al. (1954) Ind. Eng. Chem., 46 (9): 1917-1921). Such processes are cumbersome, can be polluting and typically produce only a limited variety of unsaturated fatty alcohol products.

Fortunately however, biological methods are available for the direct production of 5-dodecene-1,3-diol. Thus, in exemplary embodiments, 5-dodecene-1,3-diol is made using biological methods as disclosed e.g., in WO 2016/011430 A1 and as disclosed in detail in Example 1 herein below.

Briefly, preparation of 5-dodecene-1,3-diol may be carried out in recombinant host cells e.g., bacterial cells engineered to produce 1,3-diols by utilizing nucleic acids and their corresponding polypeptides of enzymatic function in order to modify enzymatic pathways for the in vivo production of desirable compounds such as e.g., 5-dodecene-1,3-diol. The enzymatic polypeptides are identified herein below by Enzyme Accession Numbers (EC Numbers).

WO 2016/011430 A1 discloses enzymatic pathways that are engineered to produce 1,3-diols. An exemplary pathway for the production of 5-dodecene-1,3-diol utilizes a 3' hydroxy acyl carrier protein (ACP) carrying an acyl intermediate (e.g., acyl-ACP or a 3-hydroxy acyl-ACP) which is converted to a 1,3-diol by way of a 3' hydroxy fatty acid (3'-OH FA) and a 3' hydroxy fatty aldehyde (3'-OH fatty aldehyde) as intermediates. Without being bound by theory it is believed that a simple carbon source such as glucose is first converted to a 3' hydroxy acyl-ACP by the microbial organism (e.g., *Escherichia, Bacillus, Lactobacillus*, etc). Thus, in one embodiment, the acyl-ACP or 3' hydroxy acyl-ACP that initiates the engineered enzymatic pathway is produced by the native pathway of the microbial organism. In exemplary embodiments the 3' hydroxy acyl-ACP is converted to an intermediate such as 3'-OH FA by an enzyme that has thioesterase (TE) activity (EC 3.1.2.- or EC 3.1.2.14 or EC 3.1.1.5). The intermediate 3'-OH FA is then converted to another intermediate such as 3' OH aldehyde by an enzyme that has carboxylic acid reductase (CAR) activity (E.C. 1.2.99.6). An enzyme that has alcohol dehydrogenase (ADH) or aldehyde reductase (AR) activity (E.C. 1.1.1.1 or E.C. 1.1.1.2) then converts the 3' OH aldehyde into a 1,3-diol.

In other embodiments, the 3' hydroxy acyl-ACP is converted to an intermediate such as 3'-OH fatty aldehyde by an enzyme that has acyl-ACP reductase (AAR, E.C. 1.2.1.42) activity. The production of fatty alcohols and/or fatty aldehydes by AAR may be enhanced through the heterologous expression of a gene called accABCD which codes for an acetyl-CoA carboxylase. An enzyme that has alcohol dehydrogenase (ADH) or aldehyde reductase (AR) activity (E.C. 1.1.1.1 or E.C. 1.1.1.2) can then convert the 3'-OH aldehyde into a fatty diol such as a 1,3-diol. Thus, the present disclosure provides recombinant microorganisms that can efficiently and selectively produce 1,3-fatty-diols e.g., 5-dodecene-1,3-diol, in vivo. It should be noted that most cells natively produce enzymes capable of reducing aldehydes, as they can be cytotoxic. Accordingly, the heterologous expression of AR and ADH may not be required for the production of fatty alcohols and diols, but they may improve the efficiency with which fatty diols are produced.

Thus, using the methods disclosed herein saturated and unsaturated 1,3-fatty-diols are produced. Exemplary 1,3-fatty-diols include, e.g., $C_5$ 1,3 fatty-diols (e.g., 1,3-pentanediol); $C_6$ 1,3 fatty-diols (e.g., 1,3-hexanediol); $C_7$ 1,3 fatty-diols (e.g., 1,3-heptanediol); $C_8$ 1,3 fatty-diols (e.g., 1,3-octanediol); $C_9$ 1,3 fatty-diols (e.g., 1,3-nonanediol); $C_{10}$ 1,3 fatty-diols (e.g., 1,3-decanediol); $C_{11}$ 1,3 fatty-diols (e.g., 1,3-undecanediol); $C_{12}$ 1,3 fatty-diols (e.g., 1,3-dodecanediol, 5-dodecene-1,3-diol); $C_{13}$ 1,3 fatty-diols (e.g., 1,3-tridecanediol); $C_{14}$ 1,3 fatty-diols (e.g., 1,3-tetradecanediol, 7-tetradecene-1,3-diol); $C_{15}$ 1,3 fatty-diols (e.g., 1,3-pentadecanediol); $C_{16}$ 1,3 fatty-diols (e.g., 1,3-hexadecanediol, 9-hexadecene-1,3-diol); $C_{17}$ 1,3 fatty-diols (e.g., 1,3-heptadecanediol); $C_{18}$ 1,3 fatty-diols (e.g., 1,3-octadecanediol, 11-octadecene-1,3-diol); $C_{19}$ 1,3 fatty-diols (e.g., 1,3-nonadecanediol); and the like. While mostly even chain 1,3-fatty-diols are disclosed herein, odd chain 1,3-fatty-diols are also found, such as those having 7-21 carbons, and more preferably 5-19 carbons.

In general, in exemplary embodiments, unsaturated 1,3-fatty-diols produced utilizing microbes as disclosed hereinabove carry the double bond in (Z) configuration. However, as will be discussed herein below, methods are available to rearrange the (Z) double bond of an unsaturated 1,3-fatty-diol e.g., the double bond of (Z)-5-dodecene-1,3-diol, such that the double bond is produced in (E) configuration.

For further guidance regarding biological synthesis of 1,3-fatty diols the person of ordinary skill in the art may refer e.g., to Examples 1-3 herein below and/or International Patent Application Publication WO 2016/011430 A1.

b. Chirality of 5-dodecene-1,3-diol

The 3-hydroxy functionality of the 1,3-fatty-diols disclosed herein e.g., 5-dodecene-1,3-diol, forms a stereo center at C-3, providing a point of chirality for the molecule. As noted above, chirality can be a useful molecular attribute in defining molecular applications including, e.g., polymer performance, bioactivity, pharmaceutical potency, and the like.

The stereoisomer of a 1,3-fatty-diol that is produced by a microorganism depends on the selectivity of the fatty acid biosynthesis pathway (FAS) from which it is produced. By manipulating which FAS enzymes are responsible for synthesis of a 1,3-fatty-diol e.g., 5-dodecene-1,3-diol, the chirality of the resulting 1,3-fatty-diol can be controlled.

For example, in an exemplary embodiment, the native *E. coli* FAS is exploited to produce the (R) enantiomer of an unsaturated-1,3-fatty-diol e.g., 5-dodecene-1,3-diol. In this embodiment, the chiral center of the unsaturated 1,3-fatty-diol is created by the activity of by 3-ketoacyl-ACP reductase, an enzyme encoded by the FabG gene in *E. coli*. The activity of 3-ketoacyl-ACP reductase produces (R)-3-hydroxyl acyl ACP which can then enter the engineered enzymatic pathway(s) discussed above in Section II a.

In other exemplary embodiments, the beta-oxidation pathway is exploited to produce the (S) enantiomer of an unsaturated 1,3-fatty-diol e.g., 5-dodecene-1,3-diol. In this embodiment, the (S) enantiomer of the unsaturated 1,3-fatty-diol is prepared by causing an accumulation of (S)-3-hydroxy acyl CoA which is an intermediate in the degradation of fatty acids through the beta-oxidation pathway. The excess (S)-3-hydroxy-acyl CoA is then converted to the (S) enantiomer of the unsaturated 1,3-fatty-diol through the action of fatty alcohol forming polypeptides.

Therefore, in an exemplary embodiment, to prepare the (S) enantiomer of an unsaturated 1,3-fatty-diol e.g., 5-dodecene-1,3-diol, available free fatty acids are first converted to acyl-CoAs by acyl-CoA synthase, a reaction catalyzed by FadD in *E. coli* (and homologs in other microorganisms). The resulting acyl-CoAs are then oxidized to trans-2-enoyl-CoA by fatty acyl-CoA dehydrogenase, a reaction catalyzed by FadE in *E. coli* (and homologs in other microorganisms). The resulting trans-2-enoyl-CoA is then hydrated to (S)-3-hydroxy-acyl-CoA by 2-trans-enoyl-CoA hydratase/(S)-3-hydroxy-acyl-CoA dehydratase, a reaction catalyzed by FadB in *E. coli* (and homologs in other microorganisms).

In the wild-type beta-oxidation pathway, (S)-3-hydroxy-acyl-CoA is then further oxidized to 3-keto-acyl-CoA by 3-keto-acyl-CoA dehydrogenase, a reaction also catalyzed by FadB in *E. coli* (and homologs in other microorganisms). The resulting 3-keto-acyl-CoA is thiolyzed to acyl-CoA and acetyl-CoA by 3-ketoacyl-CoA thiolase, a reaction catalyzed by FadA in *E. coli* (and homologs in other microorganisms).

In one exemplary embodiment, accumulation of (S)-3-hydroxy-acyl-CoA, is caused by selectively blocking the dehydrogenase activity of 3-keto-acyl-CoA dehydrogenase (FadB) to prevent the oxidation of (S)-3-hydroxy-acyl-CoA to 3-keto-acyl-CoA. In exemplary embodiments, selective blocking of the (S)-3-hydroxy-acyl-CoA dehydrogenase activity of FadB is achieved by mutation of Histidine 450 in the *E. coli* FadB gene (see e.g., He XY and Yang SY (1996) Biochemistry 35(29):9625-9630). (S)-3-hydroxy-acyl CoA accumulated in the cell is then converted to the (S) enantiomer of the unsaturated 1,3-fatty-diol e.g., (S)-5-dodecene-1,3-diol, through the action of fatty alcohol forming polypeptides, such as those disclosed e.g., in WO 2016/011430 A1.

Determination/confirmation of the resulting enantiomer configuration is achieved by any method known in the art e.g., by non-chromatographic techniques as polarimetry, by nuclear magnetic resonance, isotopic dilution, calorimetry, and enzyme techniques. These techniques require pure samples, and no separation of enantiomers is involved. Quantitation (which does not require pure samples) and separation of enantiomers can be done simultaneously by chiral chromatography such as gas chromatography (GC) or high performance liquid chromatography (HPLC) using chiral columns (see e.g., *Stereochemistry of Organic Compounds*, Ernest L. Elil and Sanuel H. Wilen, 1994, John Wiley & Sons, Inc.). The chiral purity of products can be identified using chiral chromatographic methods such as chiral HPLC or LC/MS (see e.g., US Patent Application Publication Nos. US2008/0248539A1 and US2013/0052699A1).

c. Fermentation and Production of 1,3-Fatty Diols

As used herein, fermentation broadly refers to the conversion of organic materials into target substances by recombinant host cells. For example, this includes the conversion of a carbon source by recombinant host cells into fatty acid derivatives such as 1,3-fatty diols by propagating a culture of the recombinant host cells in a media comprising the carbon source. The conditions permissive for the production of the target substances such as 1,3-fatty diols e.g., 5-dodecene-1,3-diol are any conditions that allow a host cell to produce a desired product, such as a 1,3-fatty diol composition. Suitable conditions include, for example, typical fermentation conditions see e.g., *Principles of Fermentation Technology*, 3rd Edition (2016) supra; *Fermentation Microbiology and Biotechnology*, 2nd Edition, (2007) supra.

Fermentation conditions can include many parameters, including but not limited to temperature ranges, pH levels, levels of aeration, feed rates and media composition. Each of these conditions, individually and in combination, allows the host cell to grow. Fermentation can be aerobic, anaerobic, or variations thereof (such as micro-aerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the host cells engineered to produce 1,3-fatty-diols can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express desired polynucleotide sequences, such as a polynucleotides encoding polypeptides having specific enzymatic activity (e.g., thioesterase (TE), carboxylic acid reductase (CAR), alcohol dehydrogenase (ADH), fatty acyl CoA/ACP reductase (FAR), acyl-CoA reductase (ACR), acyl CoA carboxylase (ACC) and/or acyl ACP/CoA reductase (AAR) enzymatic activity). For large scale production, the engineered host cells can be grown in cultures having a volume batches of about 10 L, 100 L, 1000 L, 10,000 L, 100,000 L, 1,000,000 L or larger; fermented; and induced to express any desired polynucleotide sequence. The 1,3-fatty diol compositions described herein can be found in the extracellular environment of the recombinant host cell culture and can be readily isolated from the culture medium. A fatty acid derivative such as a 1,3-fatty diol e.g., 5-dodecene-1,3-diol and/or a fatty alcohol may be secreted by the recombinant host cell, transported into the extracellular environment or passively transferred into the extracellular environment of the recombinant host cell culture. The 1,3-fatty diol composition may be isolated from a recombinant host cell culture using routine methods known in the art (see e.g., Example 2 herein below).

Exemplary microorganisms suitable for use as production host cells include e.g., bacteria, cyanobacteria, yeast, algae, or filamentous fungi, etc. To produce 1,3-fatty diols, production host cells (or equivalently, host cells) are engineered to comprise fatty acid biosynthesis pathways that are modified relative to non-engineered or native host cells e.g., engineered as discussed above in Section II.a. and as disclosed in WO 2016/011430 A1. Production hosts engineered to comprise modified fatty acid biosynthesis pathways are able to efficiently convert glucose or other renewable feedstocks into fatty acid derivatives, including fatty alcohols and 1,3-fatty diols e.g., 5-dodecene-1,3-diol. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439).

In some exemplary embodiments, a production host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L.

In some exemplary embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one exemplary embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, pectin, xylan, sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example 1,3 diols may be produced by recombinant cyanobacteria growing photosynthetically and using $CO_2$ as carbon source. In certain embodiments, the carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some exemplary embodiments, the 1,3-fatty diol e.g., 5-dodecene-1,3-diol, is produced at a concentration of about 0.5 g/L to about 40 g/L. In some embodiments, the 1,3-fatty diol is produced at a concentration of about 1 g/L or more (e.g., about 1 g/L or more, about 10 g/L or more, about 20 g/L or more, about 50 g/L or more, about 100 g/L or more). In some embodiments, the 1,3-fatty diol is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In other exemplary embodiments, the 1,3-fatty diol is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a 1,3-fatty diol (e.g., 1,3-diol) is produced at a titer of more than 100 g/L, more than 200 g/L, more than 300 g/L, or higher, such as 500 g/L, 700 g/L, 1000 g/L, 1200 g/L, 1500 g/L, or 2000 g/L. A preferred titer of a 1,3-fatty diol such as a 1,3-diol produced by a recombinant host cell according to the methods of the disclosure is from 5 g/L to 200 g/L, 10 g/L to 150 g/L, 20 g/L to 120 g/L and 30 g/L to 100 g/L, 100 g/L to 150 g/L, and 120 g/L to 180 g/L. In one embodiment, the titer of a 1,3-fatty diol such as a 1,3-diol produced by a recombinant host cell according to the methods of the disclosure is about 1 g/L to about 250 g/L and more particularly, 90 g/L to about 120 g/L. The titer may refer to a particular 1,3-diol or a combination of 1,3-diols of different chain length or different functionalities such as e.g., a mixture of saturated and unsaturated 1,3-fatty-diols produced by a given recombinant host cell culture.

In other exemplary embodiments, the host cells engineered to produce a 1,3-fatty diol such as e.g., 5-dodecene-1,3-diol according to the methods of the disclosure have a yield of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, or at least 40% or a range bounded by any two of the foregoing values. In other embodiments, a 1,3-fatty diol such as e.g., 5-dodecene-1,3-diol is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a 1,3-fatty diol such as a 1,3-diol produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of a 1,3-fatty diol such as a 1,3-diol produced by the recombinant host cell is about 10% to about 40%. In another particular embodiment, the yield of a 1,3-fatty diol such as a 1,3-diol produced by the recombinant host cell is about 25% to about 30%. The yield may refer to a particular 1,3-fatty diol such as 5-dodecene-1,3-diol or a combination of 1,3-diols produced by a given recombinant host cell culture. In addition, the yield will also be dependent on the feedstock used.

In some exemplary embodiments, the productivity of the host cells engineered to produce a 1,3-fatty diol such as e.g., 5-dodecene-1,3-diol according to the methods of the disclosure is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of a 1,3-fatty diol such as a 1,3-diol produced by a recombinant host cell according to the methods of the disclosure may be from 500 mg/L/hour to 2500 mg/L/hour, or from 700 mg/L/hour to 2000 mg/L/hour. In one exemplary embodiment, the productivity is about 0.7 mg/L/h to about 3 g/L/h. Productivity as used herein, refers to a particular 1,3-fatty diol such as e.g., 5-dodecene-1,3-diol produced by a given recombinant host cell culture.

In some exemplary embodiments, the host cell used in the fermentation procedures discussed herein (supra) is a mammalian cell, plant cell, insect cell, yeast cell, fungus cell, filamentous fungi cell, an algal cell, a cyanobacterial cell, and bacterial cell. In particular embodiments, the host cell is selected from the genus *Escherichia, Bacillus, Pseudomonas, Lactobacillus, Rhodococcus, Synechococcus, Synechoystis, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In other exemplary embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other exemplary embodiments, the host cell is a *Pseudomonas putida* cell. In certain embodiments, the host cell is a *Synechococcus* sp. PCC7002, *Synechococcus elongatus* PCC 7942, *Synechoystis* sp. PCC 6803, *Synechococcus elongatus* PCC6301, *Prochlorococcus marinus* CCMP1986 (MED4), *Anabaena variabilis* ATCC29413, *Nostoc punctiforme* ATCC29133 (PCC73102), *Gloeobacter violaceus* ATCC29082 (PCC7421), *Nostoc* sp. ATCC27893 (PCC7120), *Cyanothece* sp. PCC7425 (29141), *Cyanothece* sp. ATCC51442, or *Synechococcus* sp. ATCC27264 (PCC7002). In other exemplary embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In other exemplary embodiments, the host cell is an Actinomycetes cell. In still other exemplary embodiments, the host cell is a *Streptomyces lividans* cell or a *Streptomyces murinus* cell. In other embodiments, the host cell is a *Saccharomyces cerevisiae* cell.

In still other exemplary embodiments, the host cell is a cell from a eukaryotic plant, algae, cyanobacterium, greensulfur bacterium, green non-sulfur bacterium, purple sulfur bacterium, purple non-sulfur bacterium, extremophile, yeast, fungus, engineered organisms thereof, or a synthetic organism. In some exemplary embodiments, the host cell is a cell from *Arabidopsis thaliana, Panicum virgatums, Miscanthus giganteus, Zea mays, botryococcuse braunii, Chalamydomonas reinhardtii, Dunaliela salina, Thermosynechococcus elongatus, Synechococcus elongatus, Synechococcus* sp., *Synechocystis* sp., *Chlorobium tepidum, Chloroflexus auranticus, Chromatiumm vinosum, Rhodospirillum rubrum, Rhodobacter capsulatus, Rhodopseudomonas palusris, Clostridium ljungdahlii, Clostridiuthermocellum,* or *Pencillium chrysogenum*. In some other exemplary embodiments, the host cell is from *Pichia pastories, Saccharomyces cerevisiae, Yarrowia lipolytica, Schizosaccharomyces pombe, Pseudomonas fluorescens, Pseudomonas putida* or *Zymomonas mobilis*. In still further exemplary embodiments, the host cell is a cell from *Synechococcus* sp. PCC 7002, *Synechococcus* sp. PCC 7942, or *Synechocystis* sp. PCC6803. In some exemplary embodiments, the host cell is a CHO cell, a COS cell, a VERO cell, a BHK cell, a HeLa cell, a Cv1 cell, an MDCK cell, a 293 cell, a 3T3 cell, or a PC12 cell. In some exemplary embodiments, the host cell is an *E. coli* cell. In some exemplary embodiments, the *E. coli* cell is a strain B, a strain C, a strain K, or a strain W *E. coli* cell.

d. Metathesis

As discussed above, the double bond of an unsaturated 1,3-fatty-diol e.g., 5-dodecene-1,3-diol, produced by recombinant host cells engineered to produce 1,3-fatty-diols is predominantly in (Z) configuration.

U.S. Pat. No. 9,163,267 teaches methods for producing an olefin by contacting a composition comprising at least one omega-7-olefinic fatty acid or derivative thereof with a cross metathesis catalyst under conditions allowing a cross metathesis transformation, wherein the at least one omega-7-olefinic fatty acid or derivative thereof was produced in a genetically engineered microorganism. Thus, in exemplary embodiments, methods such as those disclosed in U.S. Pat. No. 9,163,267 are used to prepare a (E) isomer of an unsaturated (Z)-1,3-fatty-diol e.g., (E) isomer of 5-dodecene-1,3-diol, made using engineered microbes as disclosed herein above. As is well known in the art, in cross metathesis reactions, the (Z)-(E) selectivity is typically biased towards the formation of the (E)-isomer (see e.g., Naeimeh Bahri-Laleh et al., (2011) Beilstein J. Org. Chem. 7:40-45).

III. Compositions and Formulations of 1,3-Fatty Diols

Bioproducts e.g., compositions comprising 5-dodecene-1,3-diol produced utilizing engineered microbes as discussed above in Sections II a-II d., are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}$C dating. Additionally, the specific source of biosourced carbon (e.g., glucose vs. glycerol) can be determined by dual carbon-isotopic fingerprinting by methods known in the art (see, e.g., U.S. Pat. No. 7,169,588, WO 2016/011430 A1, etc.).

The following examples are offered to illustrate, but not to limit the invention.

EXAMPLES

Example 1

The following Example illustrates production of 5-dodecen-1,3-diol by fermentation. 5-dodecen-1,3-diol was produced by fermentation using an *E. coli* strain engineered for the production fatty alcohols and 1,3 diols. These 1,3-fatty-diols were then refined from the resulting fermentation broth.

Strain stNH1282, which is a derivative of strain MG1655 that was modified as disclosed e.g., in WO 2016/011430 A1, to attenuate the activity of FadE (involved in fatty acid degradation) and engineered to overexpress a thioesterase specific for C12 chain lengths (such as FatB1), EntD (a phosphopantethienyl transferease), CarB (a carboxylic acid reductase), and AlrA-ADP1 (an alcohol dehydrogenase), was inoculated from a 1 mL glycerol freezer stock into LB medium (100 mL) containing spectinomycin (115 mg/L) and shaken at 32° C. for 6-8 hours until the culture OD reached 3-6.

Two seed bioreactors were prepped with four liters of seed media 2 (Table I) and then inoculated at 1.0% (v/v) with this LB culture, and cultivated using the following bioreactor parameters: pH=6.9 with $NH_4OH$ addition, airflow=0.5 v/v/m, (dissolved oxygen) DO=30% of saturation, and temp=33° C. These bioreactors were run overnight (~16 hours), until the glucose was exhausted, and the culture optical density (OD) was between 20 and 30 absorption units (AU).

TABLE I

Bioreactor Seed Media Composition.

| Component | Concentration |
|---|---|
| $(NH_4)_2SO_4$ (g/L) | 0.5 |
| $KH_2PO_4$ (g/L) | 2 |
| TM4 Solution (ml/L) - Table III. | 2.5 |
| $CaCl_2$—$2H_2O$ (mg/L) | 140 |
| Fe citrate mg/L | 80 |
| NaCl (g/L) | 1 |
| $MgSO_4$—$7H_2O$ (g/L) | 0.5 |
| Trace Vitamin Solution (ml/L) - Table IV. | 0.625 |
| Thiamine (mg/L) | 0.1 |
| Post sterile additions | |
| Glucose (g/L) | 40 |
| Spec | 1 |
| Inoculum (ml/L) | 10 |

The 700 liter (L) production bioreactor was initially batched with 250 L of production media (Table II), and inoculated with 7.5 L of the seed bioreactors (3% volume/volume (v/v)). This bioreactor was cultivated using the following bioreactor parameters: pH=6.9 with $NH_4OH$ addition, airflow=0.5 volume/volume/minute (v/v/m), DO=15% of saturation (with one bar of backpressure), and temp=33° C.

Culture was induced by bringing the medium to 0.5 mM IPTG when the OD was greater than 10 AU. After depletion of the initial glucose in the tank, the bioreactor was fed a glucose solution (62% weight/weight (w/w)) at a rate of 10 g/L (initial volume)/hour for a duration of one hour. Subsequent hour-long glucose feeds were initiated upon glucose depletion, triggered by a rise in the dissolved oxygen in the tank. This was continued through the fermentation. Any foaming was controlled by automated addition of Xiameter 1410® (Dow Corning). The run was terminated after 72 hours, and the culture broth collected by centrifugation.

TABLE II

Production Bioreactor Media Composition.

| Component | Concentration |
|---|---|
| $(NH_4)_2SO_4$ (g/L) | 0.5 |
| $KH_2PO_4$ (g/L) | 2 |
| TM4 Solution (ml/L) - Table III. | 2.5 |
| $CaCl_2$—$2H_2O$ (mg/L) | 140 |
| Fe citrate mg/L | 80 |
| NaCl (g/L) | 1 |
| $MgSO_4$—$7H_2O$ (g/L) | 2.2 |
| Trace Vitamin Solution (ml/L) - Table IV. | 0.625 |
| Thiamine (mg/L) | 0.1 |
| Post sterile additions | |
| Glucose (g/L) | 10 |
| Inoculum (ml/L) | 32 |

TABLE III

Trace Vitamins Solution.

| Component | Concentration |
|---|---|
| $ZnCl_2$ | 4 g/L |
| $CaCl_2 \cdot 2H_2O$ | 8 g/L |
| $Na_2MoO_4 \cdot 2H_2O$ | 8 g/L |
| $CuSO_4 \cdot 5H_2O$ | 7.6 g/L |
| $H_3BO_3$ | 2.0 g/L |
| HCl (concentrated) | 8 mL/L |

TABLE IV

Trace Vitamins Solution.

| Component | Concentration |
|---|---|
| Riboflavin | 0.06 g/L |
| pantothenic acid | 5.4 g/L |
| Niacin | 6 g/L |
| Pyridoxine | 1.4 g/L |
| Biotin | 0.06 g/L |
| Folic acid | 0.01 g/L |

Example 2

The following Example illustrates refinement of 1,3 diol from the centrifuged fermentation broth.

Figure 1B:
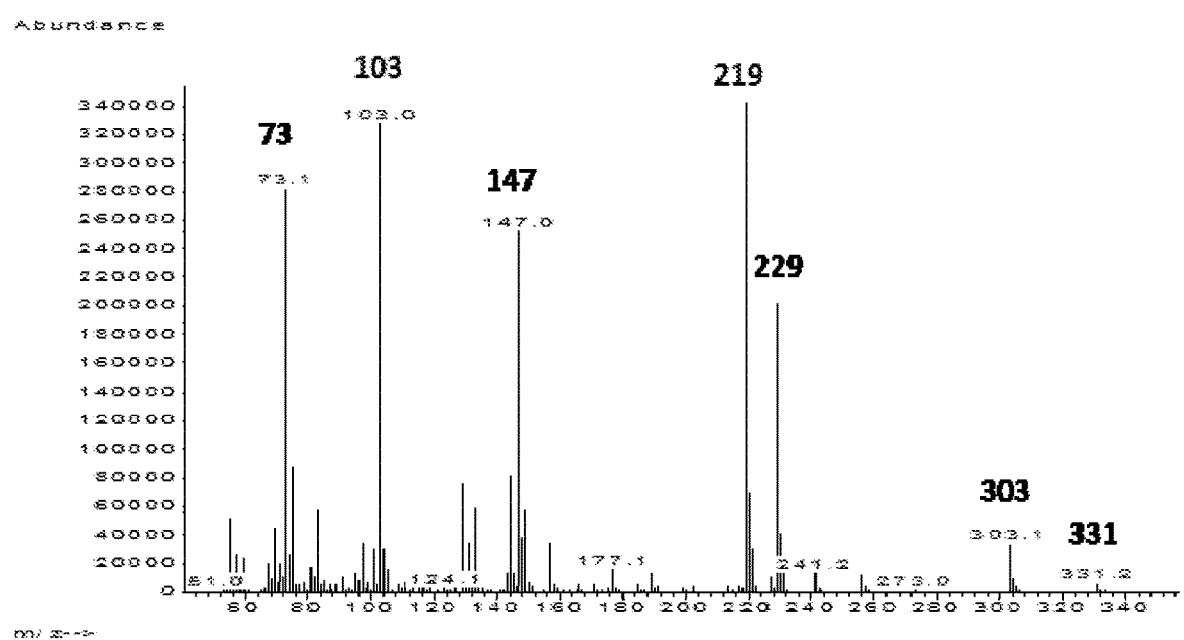
FIG. 1B shows the experimental mass spectrum fragmentation pattern of 1,3-dodedcane diol trimethylsilyl ether. Note the distinguishing ions of 331 (MW-15), 229 and 219 for the saturated diol adducts.
Figure 2A:
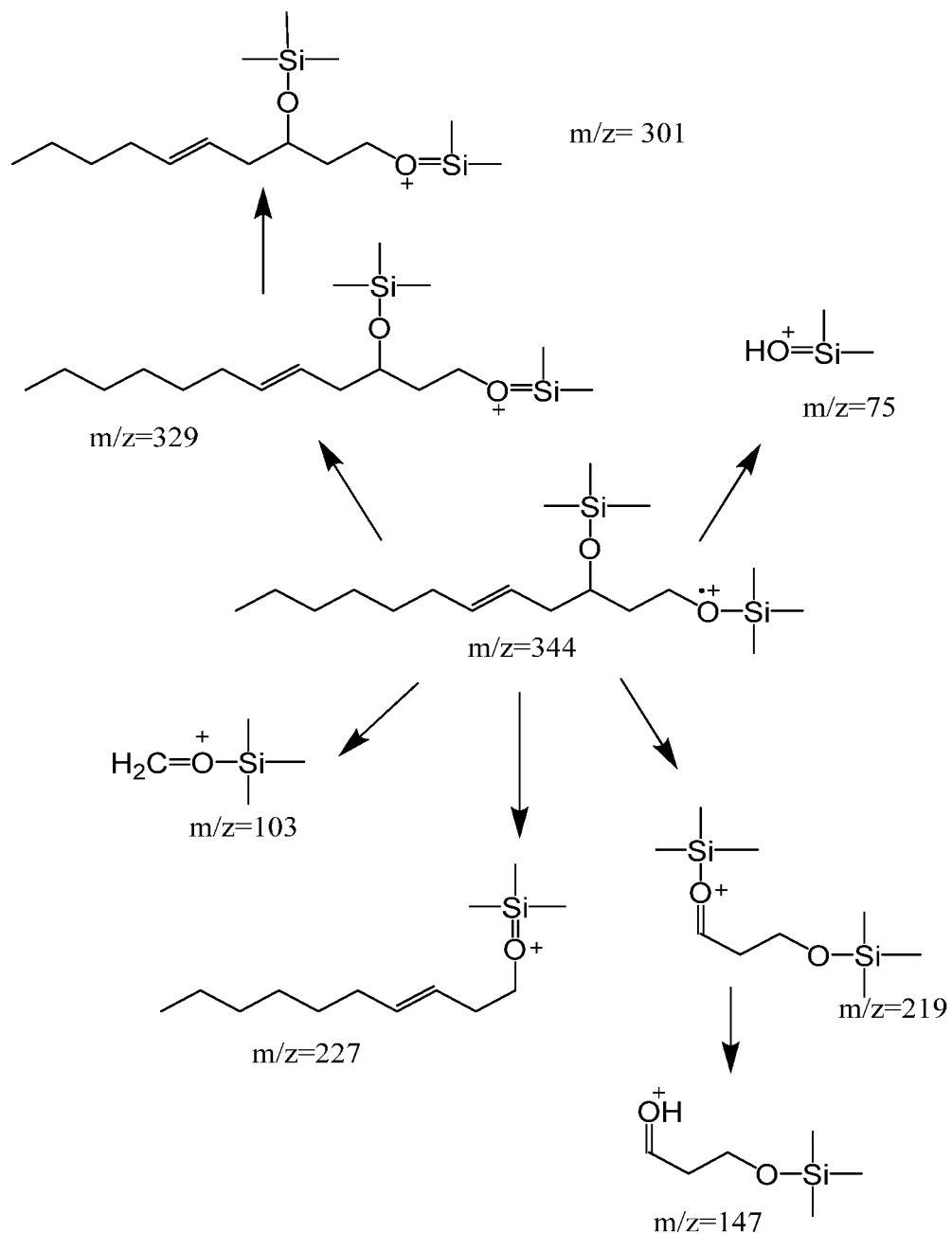
FIG. 2A Illustrates schematically the fragment ions formed from fragmentation of 5-dodecene-1,3-diol trimethylsilyl ether. In the schematic illustration of the fragment ions, the double bond is shown as (E). However, the mixture is of both (Z) and (E). Indeed, the fermentation produces predominantly 5-(Z)-dodecene-1,3-diol as a result of the unique fatty acid metabolism.
Figure 2B:
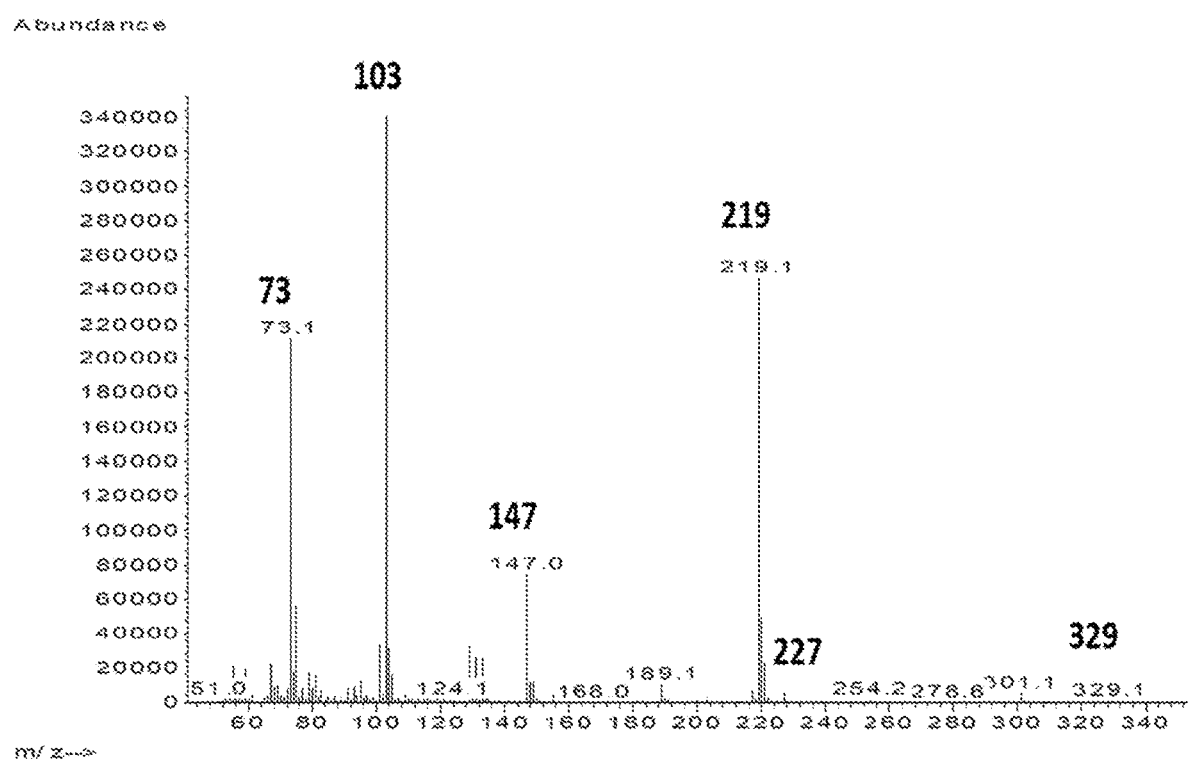
FIG. 2B shows the experimental mass spectrum fragmentation pattern of 5-dodecene-1,3-diol trimethylsilyl ether. Note the distinguishing ions of the 329 (MW-15), 227, 219 for the unsaturated diol adducts.

The product of the fermentation described above in Example 1 was a mixture of three phases, an organic phase rich in fatty alcohols and 1,3 diols, an aqueous phase containing spent fermentation media, and a solid phase containing the E. coli biomass. Upon centrifugation the light organic phase was collected. This material was then deacidified using alkaline refining and moisture drying. The resulting deacidified oil was then fractionated by distillation, and fractions rich in 5-dodecane-1,3-diol and 5-dodecene-1,3 diol were collected and pooled. The composition of fatty alcohols and 1,3 diols in the enriched pool was determined by Gas Chromatography and Mass Spectroscopy as described herein below in Example 3, and is shown in Table V. The mass spectra of the 5-dodecane-1,3 diol and 5-dodecene-1,3 diols, which were the predominant components, are shown in FIG. 1 and FIG. 2, respectively.

TABLE V

Certificate of analysis of the 1,3-diol enriched distillation fraction.

| Acid Value | mg KOH/g | 0.05 |
|---|---|---|
| Total Saponification Value | mg KOH/g | 4.01 |
| Ester Saponification Value | mg KOH/g | 3.96 |
| Carbonyl | ppm | 1008 |
| Iodine Value | cg $I_2$/g | N/A |
| Moisture (KF) | %(w/w) | 0.05 |

TABLE V-continued

Certificate of analysis of the 1,3-diol enriched distillation fraction.

| Appearance | Visual | Light yellow Liquid |
|---|---|---|
| APHA color | | N/A |
| Melting Point | °C. | N/A |
| Viscosity (dynamic) at 20° C. | mPa*s | N/A |
| Refractive Index @ 20° C. | | N/A |
| Specific Gravity @ 25° C. | g/ml | N/A |
| Total 1,3-diols | %(w/w) | 94.2 |
| 1,3-C12:1 diol | %(w/w) | 29.9 |
| 1,3-C12:0 diol | %(w/w) | 64.3 |
| Total Fatty alcohols | %(w/w) | 3.6 |
| C14:1 fatty alcohol | %(w/w) | 0.2 |
| C16:1 fatty alcohol | %(w/w) | 3.1 |
| C16:0 fatty alcohol | %(w/w) | 0.3 |
| Total FFA* | %(w/w) | 0.02 |

Example 3

The following Example illustrates an exemplary method for the analytical evaluation of fatty alcohols and 1,3 diols using gas chromatography (GC) and mass spectroscopy (MS).

The sample e.g., the 1,3 diol enriched distillation fraction described above in Example 2, is reacted with a 1:1 mixture of (N,O-Bis(trimethylsilyl)trifluoroacetamide (BSTFA)+ (1% Trimethylchlorosilane (TMCS)): toluene to form the Silyl Ethers of the alcohols. Hydrocarbons, methyl esters and aldehydes are not derivitized. The sample is then analyzed by a fast temperature ramp method employing a narrow-bore column. The GC program calculates the weight percent of the sample components by comparing the sample's response factors to those of the standard using tridecanoic acid methyl ester as an internal standard. The results of the oil analysis of the 1,3 diol enriched fraction of Example 2 is shown in Table V. The identification of each compound eluting from the GC is identified by its retention time and mass spectra. The mass spectra of the 1,3-diols and a diagrammatic scheme showing the possible silyl-ether derivatized ions are shown in FIG. 1 and FIG. 2.

Example 4

The following Example illustrates synthesis of (S)-2-[2-(benzyloxy)ethyl]oxirane which is useful for the preparation of 5-dodecene-1,3-diol via the chemical synthesis route disclosed herein below in Example 5. This is a prophetic Example.

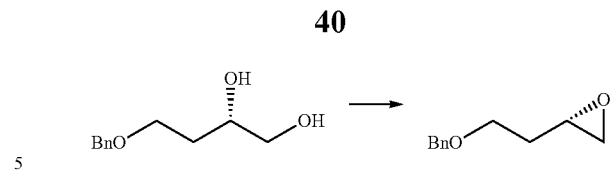

(S)-2-[2-(benzyloxy)ethyl]oxirane will be prepared via a literature procedure (see e.g., Cink, R. D.; Forsyth, C. J. *J. Org. Chem* 1995, 60, 8122). Briefly, to a magnetically stirred solution of S-4-(benzyloxy)butane-1,2-diol (207 mg, 1.05 mmol, CAS #69985-32-6) in THF (10.6 mL) at 0° C. will be added NaH (63 mg, 2.6 mmol). The resulting mixture will be warmed to room temperature and stirred for 1 hour, then cooled to 0° C. before N-tosylimidazole (237 mg, 1.07 mmol) is added in three equal portions over 20 min. The mixture will be allowed to warm to room temperature and stirred for 45 min before being recooled to 0° C. Sat. aq. NH$_4$Cl and Et$_2$O (65 mL) will then be added, the separated organic phase will be washed with H$_2$O (25 mL) and brine (25 mL), and the combined aqueous layers will be extracted with Et$_2$O (2×25 mL). The combined organic layers will then be dried (Na$_2$SO$_4$), filtered, and concentrated by rotary evaporation. Chromatography (silica gel; hexanes/EtOAc 5:1) of the residue is expected to provide the desired product.

Example 5

The following Example illustrates a method for producing (R,Z)-dodec-5-ene-1,3-diol (i.e., (R,Z)-5-dodecene-1,3-diol) using a synthetic chemistry approach. This is a prophetic Example.

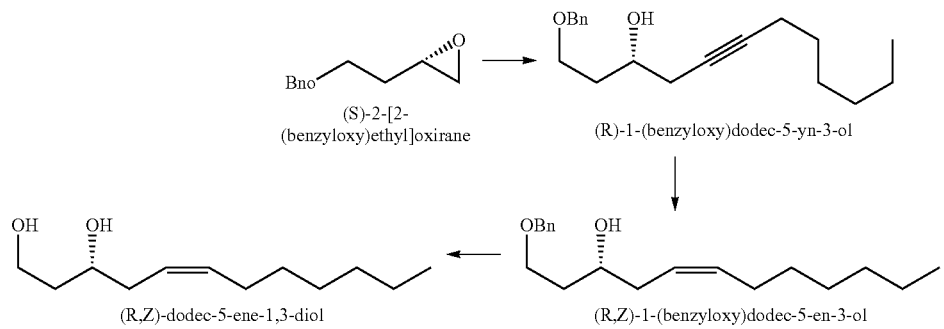

To a −78° C. solution of oct-1-yne (1.8 equiv.) in THF (0.5M) will be added 2.5M n-BuLi in hexanes (1.81 equiv.) and the resulting solution stirred for 15 min before being added to a solution of (S)-2-[2-(benzyloxy)ethyl]oxirane (1 equiv.) in THF (0.2M) at −78° C. BF$_3$·OEt$_2$ (2 equiv.) will then be added dropwise and the resulting mixture stirred at −78° C. until completion. If needed, the temperature will be slowly raised to −30° C. Sat. aq. NH$_4$Cl and Et$_2$O will then be added, the separated organic phase successively washed with H$_2$O and then brine, and the combined aqueous layers will be extracted with Et$_2$O. The combined organic layers will then be dried (Na$_2$SO$_4$), filtered, and concentrated by rotary evaporation. Chromatography (silica gel; hexanes/EtOAc) of the residue will then be used to provide (R)-1-(benzyloxy)dodec-5-yn-3-ol.

(R)-1-(benzyloxy)dodec-5-yn-3-ol will then taken up in hexane to generate a 0.2 M mixture in a flask, to which freshly prepared Lindlar catalyst (see Lindlar, H.; Dubuis, R. *Org. Synth.* 1966, 46, 89 and using freshly precipitated calcium carbonate) will be added at 20 wt % with respect to (R)-1-(benzyloxy)dodec-5-yn-3-ol or 5% palladium on calcium carbonate (10 wt % with respect to (R)-1-(benzyloxy)dodec-5-yn-3-ol) and freshly distilled quinolone (10 wt % with respect to (R)-1-(benzyloxy)dodec-5-yn-3-ol) will be added. The flask will be flushed three times with hydrogen, and then the mixture stirred under $H_2$ and monitored by consumption of $H_2$ and/or by gas chromatography. Upon indication of completing of the reaction (e.g., when 1 equivalent of $H_2$ is consumed), the suspension will be filtered through a pad of silica gel, whereupon the pad will be washed with diethyl ether. This organic layer will be concentrated and purified by chromatography (silica gel; hexanes/EtOAc) and is expected to provide (R,Z)-1-(benzyloxy)dodec-5-en-3-ol. [Note: it is well known that benzyl protecting groups usually survive Lindlar hydrogenations. However, to the extent the conditions provide a degree debenzylation to provide (R,Z)-dodec-5-ene-1,3-diol, this may be obtained via the chromatography step].

(R,Z)-1-(benzyloxy)dodec-5-en-3-ol will be taken up in $CH_2Cl_2$ to generate a 2 M solution and is stirred at 0° C. To this solution will be added 1.3 equivalents of neat trimethylsilyl iodide via a dry syringe. Reaction progress will be monitored by TLC. Upon completion, the reaction will be quenched by slow addition of 4 equivalents of MeOH. Sat. aq. $NH_4Cl$ and $Et_2O$ will then be added, the separated organic phase washed with $H_2O$ and brine, and the combined aqueous layers will be extracted with $Et_2O$ (2×25 mL). The combined organic layers will then be dried ($Na_2SO_4$), filtered, and concentrated by rotary evaporation. Chromatography (silica gel; hexanes/EtOAc) of the residue will then be used to provide (R,Z)-dodec-5-ene-1,3-diol.

Alternatively, the secondary alcohol of (R,Z)-1-(benzyloxy)dodec-5-en-3-ol may be protected by a tert-butyldimethylsilyl ("TBS") group prior to benzyl group cleavage and then the TBS group removed after debenzylation. Thus, to a 0.1M solution of (R,Z)-1-(benzyloxy)dodec-5-en-3-ol (1 equiv.) in $CH_2Cl_2$ will be added 2,6-lutidine (1.3 equiv.) and the mixture subsequently cooled to 0° C., whereupon tert-butyldimethylsilyl triflate (1.1 equiv.) will be added dropwise with stirring. The solution will be allowed to stir at 0° C. until completion as monitored by thin layer chromatography. Sat. aq. $NH_4Cl$ and $Et_2O$ will then be added, the separated organic phase successively washed with $H_2O$ and then brine, and the combined aqueous layers will be extracted with $Et_2O$. The combined organic layers will then be dried ($Na_2SO_4$), filtered, and concentrated by rotary evaporation. Chromatography (silica gel; hexanes/EtOAc) of the residue will then be used to provide (R,Z)-((1-(benzyloxy)dodec-5-en-3-yl)oxy)(tert-butyl)dimethylsilane.

(R,Z)-((1-(benzyloxy)dodec-5-en-3-yl)oxy)(tert-butyl)dimethylsilane will be taken up in $CH_2Cl_2$ to generate a 2.0M solution and is stirred at 0° C. To this solution will be added 1.3 equivalents of neat trimethylsilyl iodide via a dry syringe. Reaction progress will be monitored by thin layer chromatography. Upon completion, the reaction will be quenched by slow addition of 4 equivalents of MeOH. Sat. aq. $NH_4Cl$ and $Et_2O$ will then be added, the separated organic phase washed with $H_2O$ and brine, and the combined aqueous layers will be extracted with $Et_2O$ (2×25 mL). The combined organic layers will then be dried ($Na_2SO_4$), filtered, and concentrated by rotary evaporation. Chromatography (silica gel; hexanes/EtOAc) of the residue will then be used to provide (R,Z)-3-((tert-butyldimethylsilyl)oxy)dodec-5-en-1-ol.

To a stirring 2.0M solution of (R,Z)-3-((tert-butyldimethylsilyl)oxy)dodec-5-en-1-ol in THF at 0° C. will be added tetrabutylammonium fluoride (1.0 M in THF; 1.2 equiv.), whereupon the mixture will be allowed to slowly warm to room temperature and the reaction allowed to proceed to completion (monitored by thin layer chromatography). Upon completion, sat. aq. $NH_4Cl$ and $Et_2O$ will be added, the separated organic phase successively washed with $H_2O$ and then brine, and the combined aqueous layers will be extracted with $Et_2O$. The combined organic layers will then be dried ($Na_2SO_4$), filtered, and concentrated by rotary evaporation. Chromatography (silica gel; hexanes/EtOAc) of the residue will then be used to provide (R,Z)-dodec-5-ene-1,3-diol.

Example 6

The following Example illustrates an exemplary chemical synthesis method for the for the preparation of (R,Z)-tetradec-7-ene-1,3-diol. This is a prophetic Example.

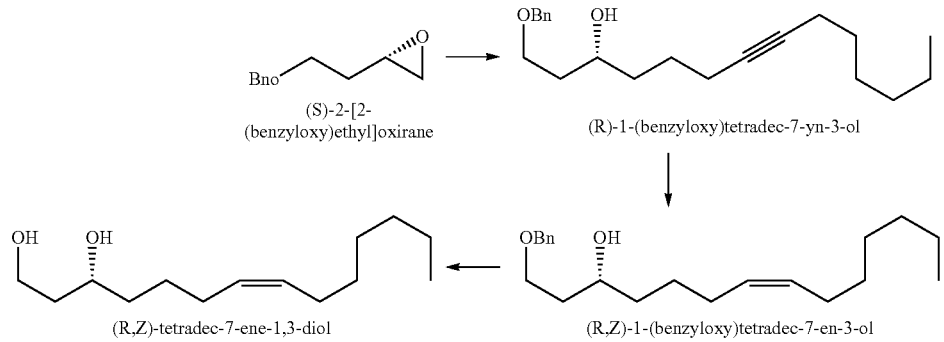

1-bromodec-3-yne may be obtained from commercial sources or may obtained via reaction of oct-1-yne with oxirane in the presence of $BF_3 \cdot OEt_2$ (see Example 5 above) to produce dec-3-yn-1-ol followed by conversion of dec-3-yn-1-ol to 1-bromodec-3-yne, for example via reaction with thionyl bromide as described in U.S. Pat. No. 9,353,090. In particular, to a stirring solution of dec-3-yn-1-ol (1 equiv.) in $CH_2Cl_2$ (0.2 M) at 0° C. will be added freshly distilled dimethyl formamide (0.5 equiv.) followed by addition of thionyl bromide (1.3 equiv.). The mixture will continue to be stirred and allowed to slowly warm to 20° C. Upon completion of the reaction (e.g., as indicated by thin layer chromatography and/or gas chromatography), $Et_2O$ and then sat. aq. $NH_4Cl$ will be added, the separated organic phase washed with $H_2O$ and brine, and the combined aqueous layers will be extracted with $Et_2O$. The combined organic layers will then be dried (Na$_2$SO$_4$), filtered, and concentrated by rotary evaporation. Chromatography (silica gel; petroleum ether/Et$_2$O) of the residue will then be used to provide 1-bromodec-3-yne.

To a 0.1 M room temperature solution of (S)-2-[2-(benzyloxy)ethyl]oxirane in THF is added CuCN (0.5 equiv), whereupon the mixture will be stirred for 5 minutes and then cooled to −40° C. To this stirred solution will be added 3.3 equivalents of a −20° C. freshly prepared dec-3-yn-1-yl magnesium bromide in THF (1.0 M; prepared from 1-bromodec-3-yne). The resulting mixture will be kept at −40° C. for about 1 hour, then warmed to 0° C. over 75 minutes. Upon completion of the reaction, sat. aq. NH$_4$Cl and Et$_2$O will then be added, the separated organic phase washed with H$_2$O and brine, and the combined aqueous layers will be extracted with Et$_2$O. The combined organic layers will then be dried (Na$_2$SO$_4$), filtered, and concentrated by rotary evaporation. Chromatography (silica gel; hexanes/EtOAc) of the residue will then be used to provide (R)-1-(benzyloxy)tetradec-7-yn-3-ol.

(R)-1-(benzyloxy)tetradec-7-yn-3-ol will then be taken up in hexane to generate a 0.2 M mixture in a flask, to which freshly prepared Lindlar catalyst (see Lindlar, H.; Dubuis, R. *Org. Synth.* 1966, 46, 89 and using freshly precipitated calcium carbonate) will be added at 20 wt % with respect to (R)-1-(benzyloxy)tetradec-7-yn-3-ol or 5% palladium on calcium carbonate (10 wt % with respect to (R)-1-(benzyloxy)tetradec-7-yn-3-ol) and freshly distilled quinolone (10 wt % with respect to (R)-1-(benzyloxy)tetradec-7-yn-3-ol) will be added. [Note: solubility may be enhanced by utilizing EtOAc as a cosolvent or in place of hexane]. The flask will be flushed three times with hydrogen, and then the mixture stirred under H$_2$ and monitored by consumption of H$_2$ and/or by gas chromatography. Upon indication of completion of the reaction (e.g., when 1 equivalent of H$_2$ is consumed), the suspension will be filtered through a pad of silica gel, whereupon the pad will be washed with diethyl ether. This organic layer will be concentrated and purified by chromatography (silica gel; hexanes/EtOAc) and is expected to provide (R,Z)-1-(benzyloxy)tetradec-7-en-3-ol. [Note: it is well known that benzyl protecting groups usually survive Lindlar hydrogenations. However, to the extent the conditions provide a degree of debenzylation to provide (R,Z)-tetradec-7-ene-1,3-diol, this may be isolated via the chromatography step].

(R,Z)-1-(benzyloxy)tetradec-7-en-3-ol will be taken up in CH$_2$Cl$_2$ to generate a 2 M solution and that will be stirred at 0° C. To this solution will be added 1.5 equivalents Et$_3$N followed by 2.3 equivalents of neat trimethylsilyl iodide via a dry syringe. Reaction progress will be monitored by TLC. Upon completion, the reaction will be quenched by slow addition of 4 equivalents of MeOH. Aq. NaHSO$_4$ (1.0 M) will then be added the mixture stirred for 15 minutes, followed by addition of Et$_2$O. The separated organic phase will then be washed with H$_2$O and brine, and the combined aqueous layers will be extracted with Et$_2$O (2×25 mL). The combined organic layers will then be dried (Na$_2$SO$_4$), filtered, and concentrated by rotary evaporation. Chromatography (silica gel; hexanes/EtOAc) of the residue will then be used to provide (R,Z)-tetradec-7-ene-1,3-diol.

Alternatively, the secondary alcohol of (R,Z)-1-(benzyloxy)tetradec-7-en-3-ol may be TBS protected followed by deprotection of the benzyl group and finally TBS-deprotected via the alternate procedure disclosed herein above in Example 5.

Example 7

The following Example illustrates an exemplary chemical synthesis method for the for the preparation of (R,Z)-tridec-6-ene-1,3-diol. This is a prophetic Example.

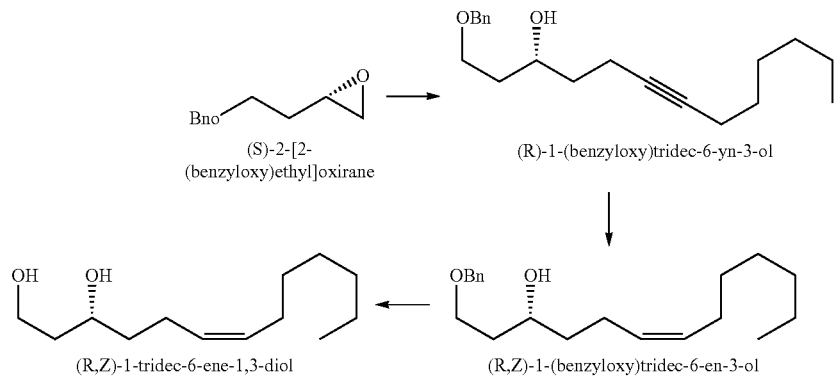

1-bromonon-2-yne (CAS #5921-74-4), used to generate non-2-yn-1-ylmagnesium bromide, may be obtained from commercial sources.

To a 0.1 M room temperature solution of (S)-2-[2-(benzyloxy)ethyl]oxirane in THF is added CuCN (0.5 equiv), whereupon the mixture will be stirred for 5 minutes and then cooled to −40° C. To this stirred solution will be added 3.3 equivalents of a −20° C. freshly prepared non-2-yn-1-yl-magnesium bromide in THF (1.0 M; prepared from 1-bromonon-2-yne). The resulting mixture will be kept at −40° C. for about 1 hour, then warmed to 0° C. over 75 minutes. Upon completion of the reaction, sat. aq. NH$_4$Cl and Et$_2$O will then be added, the separated organic phase washed with H$_2$O and brine, and the combined aqueous layers will be extracted with Et$_2$O. The combined organic layers will then be dried (Na$_2$SO$_4$), filtered, and concentrated by rotary evaporation. Chromatography (silica gel; hexanes/EtOAc) of the residue will then be used to provide (R)-1-(benzyloxy)tridec-6-yn-3-ol.

(R)-1-(benzyloxy)tridec-6-yn-3-ol will then taken up in hexane to generate a 0.2 M mixture in a flask, to which freshly prepared Lindlar catalyst (see Lindlar, H.; Dubuis, R. *Org. Synth.* 1966, 46, 89 and using freshly precipitated calcium carbonate) will be added at 20 wt % with respect to (R)-1-(benzyloxy)tridec-6-yn-3-ol or 5% palladium on calcium carbonate (10 wt % with respect to (R)-1-(benzyloxy)tridec-6-yn-3-ol) and freshly distilled quinolone (10 wt % with respect to (R)-1-(benzyloxy)tridec-6-yn-3-ol) will be added. [Note: solubility may be enhanced by utilizing EtOAc as a cosolvent or in place of hexane]. The flask will be flushed three times with hydrogen, and then the mixture stirred under $H_2$ and monitored by consumption of $H_2$ and/or by gas chromatography. Upon indication of completion of the reaction (e.g., when 1 equivalent of $H_2$ is consumed), the suspension will be filtered through a pad of silica gel, whereupon the pad will be washed with diethyl ether. This organic layer will be concentrated and purified by chromatography (silica gel; hexanes/EtOAc) and is expected to provide (R,Z)-1-(benzyloxy)tridec-6-en-3-ol. [Note: it is well known that benzyl protecting groups usually survive Lindlar hydrogenations. However, to the extent the conditions provide a degree of debenzylation to provide (R,Z)-tridec-6-ene-1,3-diol, this may be isolated via the chromatography step].

(R,Z)-1-(benzyloxy)tridec-6-en-3-ol will be taken up in $CH_2Cl_2$ to generate a 2 M solution and that will be stirred at 0° C. To this solution will be added 1.5 equivalents $Et_3N$ followed by 2.3 equivalents of neat trimethylsilyl iodide via a dry syringe. Reaction progress will be monitored by TLC. Upon completion, the reaction will be quenched by slow addition of 4 equivalents of MeOH. Aq. $NaHSO_4$ (1.0 M) will then be added the mixture stirred for 15 minutes, followed by addition of $Et_2O$. The separated organic phase will then be washed with $H_2O$ and brine, and the combined aqueous layers will be extracted with $Et_2O$ (2×25 mL). The combined organic layers will then be dried ($Na_2SO_4$), filtered, and concentrated by rotary evaporation. Chromatography (silica gel; hexanes/EtOAc) of the residue will then be used to provide (R,Z)-tridec-6-ene-1,3-diol.

Alternatively, the secondary alcohol of (R,Z)-1-(benzyloxy)tridec-6-en-3-ol may be TBS protected followed by deprotection of the benzyl group and finally TBS-deprotected via the alternate procedure disclosed herein above in Example 5.

Example 8

The following Example illustrates chemical based synthesis of (R,E)-dodec-5-ene-1,3-diol. This is a prophetic Example.

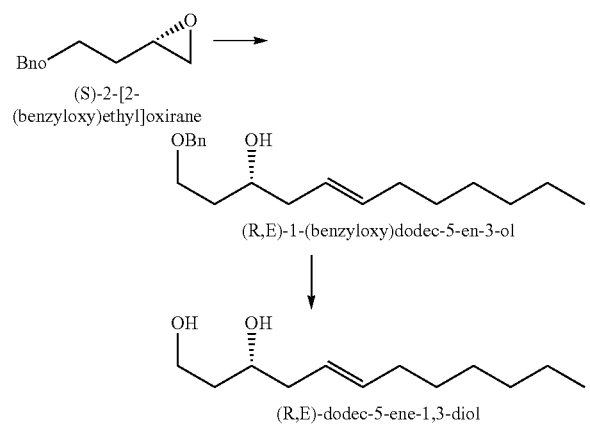

To a 0.1 M room temperature solution of (S)-2-[2-(benzyloxy)ethyl]oxirane in THF is added CuCN (0.5 equiv), whereupon the mixture will be stirred for 5 minutes and then cooled to −40° C. To this stirred solution will be added 3.3 equivalents of a −20° C. freshly prepared (E)-oct-1-en-1-yl magnesium bromide solution in THF (1.0 M). The resulting mixture will be kept at −40° C. for about 1 hour, then warmed to 0° C. over 75 minutes. Upon completion of the reaction, sat. aq. $NH_4Cl$ and $Et_2O$ will then be added, the separated organic phase washed with $H_2O$ and brine, and the combined aqueous layers will be extracted with $Et_2O$. The combined organic layers will then be dried ($Na_2SO_4$), filtered, and concentrated by rotary evaporation. Chromatography (silica gel; hexanes/EtOAc) of the residue will then be used to provide (R,E)-1-(benzyloxy)dodec-5-en-3-ol.

(R,E)-1-(benzyloxy)dodec-5-en-3-ol will be taken up in $CH_2Cl_2$ to generate a 2 M solution and is stirred at 0° C. To this solution will be added 1.5 equivalents $Et_3N$ followed by 2.3 equivalents of neat trimethylsilyl iodide via a dry syringe. Reaction progress will be monitored by TLC. Upon completion, the reaction will be quenched by slow addition of 4 equivalents of MeOH. Aq. $NaHSO_4$ (1.0 M) will then be added the mixture stirred for 15 minutes, followed by addition of $Et_2O$. The separated organic phase will then be washed with $H_2O$ and brine, and the combined aqueous layers will be extracted with $Et_2O$ (2×25 mL). The combined organic layers will then be dried ($Na_2SO_4$), filtered, and concentrated by rotary evaporation. Chromatography (silica gel; hexanes/EtOAc) of the residue will then be used to provide (R,E)-dodec-5-ene-1,3-diol.

Alternatively, the secondary alcohol of (R,E)-1-(benzyloxy)dodec-5-en-3-ol may be TBS protected followed by deprotection of the benzyl group and finally TBS-deprotected via the alternate procedure described in Example 2.

Example 9

The following Example illustrates chemical synthesis of (R)-dodecane-1,3-diol. This is a prophetic Example.

To a flask will be charged (R)-1-(benzyloxy)dodec-5-yn-3-ol (1 equiv.), Pd/C (0.01 equiv. based on Pd content), and degassed EtOAc to form a 0.1 M solution based on (R)-1-(benzyloxy)dodec-5-yn-3-ol. The flask will be flushed three times with hydrogen, and then the mixture stirred under $H_2$ and monitored by gas chromatography and/or NMR. Upon completion, the suspension will be filtered through a pad of silica gel, whereupon the pad will be washed with diethyl ether. This organic layer will be concentrated and purified by chromatography (silica gel; hexanes/EtOAc) and is expected to provide (R)-dodecane-1,3-diol.

Example 10. Exemplary Two-Step Synthesis of Glycosylated (R,Z)-Dodec-5-Ene-1,3-Diol The following Example illustrates an exemplary Two-Step Synthesis of Glycosylated (R,Z)-dodec-5-ene-1,3-diol. This is a prophetic Example.

Synthesis of glycosylated (R,Z)-dodec-5-ene-1,3-diol will also be achieved via a two-step method similar to that described by El-Sukkary et al. "Synthesis and Characterization of some Alkyl Polyglycosides Surfactants" *J. Surfact Deterg*, 2008, 11, 129-137. Briefly, to prepare glycosylated (R,Z)-dodec-5-ene-1,3-diol using the process disclosed in the El-Sukkary reference, a glucose is first reacted with butanol in the presences of p-toluenesulfonic acid to form a butyl polyglucoside. The butyl polyglucoside, now more organophilic, is then reacted with the long-chain alcohol at high temperatures and under vacuum to remove the butanol, thus, forming the desired alkyl polyglucoside. Reported yields for this procedure were 35-45%. In the present adaptation, a saccharide (e.g., glucose) will be reacted with butanol in the presences of p-toluenesulfonic acid to form a butyl saccharide, whereupon the butyl saccharide will be reacted with (R,Z)-dodec-5-ene-1,3-diol to provide glycosolated (R,Z)-dodec-5-ene-1,3-diol. When glucose is used as the saccharide, a monoglucosylated and/or a bis-glucosylated (R,Z)-dodec-5-ene-1,3-diol may be achieved based on selection of the conditions. Product yield will be measured and the product characterized by $^1$H-NMR, FTIR, and LC-MS.

Example 11

The following Example illustrates an exemplary one-step method for the preparation of (R,Z)-dodec-5-ene-1,3-diol. This is a prophetic Example.

As illustrated in the El-Sukkary reference, direct synthesis of glycosylated long-chain aliphatic hydrocarbonols is limited due to the immiscibility of the starting reagents (e.g., water-soluble glucose and organosoluble 1-octanol). This solubility problem may be mitigated by the enhanced solubility of the compounds of Formulas IA, IB, II, III, and/or IV, and thus allow for a one-step synthesis of compounds of Formulas V and/or VI.

In an exemplary embodiment comparing the water solubility of compounds is achieved by comparing their respective log P values. A person of skill in the art appreciates that log P is the logarithm of the ratio of the concentrations of the compound between n-octanol over water, as illustrated by Equation 1.

$$\log P = \log([\text{compound}]_{n\text{-}octanol}/([\text{compound}]_{water})$$  Equation 1

Thus, compounds with a higher log P are more lipophilic and less water soluble; compounds with a lower log P value are less lipophilic and more water soluble. As illustrated by calculated log P values for (R,Z)-dodec-5-ene-1,3-diol, (Z)-dodec-5-ene-1-ol, and dodecan-1-ol, (R,Z)-dodec-5-ene-1,3-diol is over an order of magnitude more water soluble than (Z)-dodec-5-ene-1-ol and almost two orders of magnitude more water soluble than dodecan-1-ol.

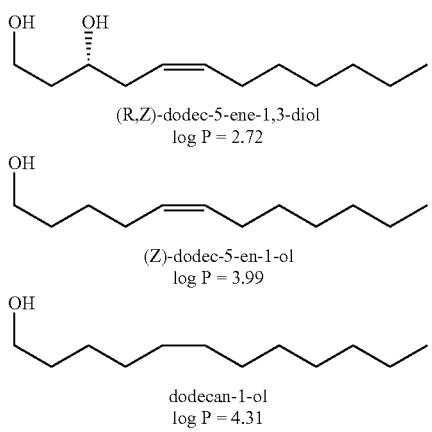

Synthesis of glycosylated compounds of Formulas V, and/or VI, via a one-step reaction will be conducted at an initial glucose scale of 25 g (approximately 240 mL total reaction volume). The molar ratio of aliphatic diol (e.g., one or more compounds of Formulas IA, IB, II, and/or III) to glucose will be set to 6:1 and the reaction temperature set to about 120° C. Variations to reaction conditions to produce different glycosylated products of Formulas V, and/or VI will include variation of the p-toluenesulfonic acid catalyst concentration and time of reaction. Product yields will be measured and the products characterized by $^1$H-NMR, FTIR, and LC-MS.

As is apparent to one of skill in the art, various modifications and variations of the above aspects and embodiments can be made without departing from the spirit and scope of this disclosure. Such modifications and variations are thus within the scope of this disclosure.

I claim:
1. A compound having a structure according to Formula V

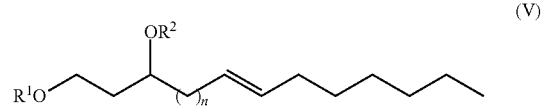

stereoisomers thereof, and pharmaceutical salts thereof, wherein $R^1$ and $R^2$ are independently selected from the group consisting of H, a monosaccharide, a disaccharide, a trisaccharide, and a polysaccharide, wherein each of the monosaccharide, disaccharide, trisaccharide or polysaccharide is bound at an anomeric carbon; and wherein $R^1$ and $R^2$ are not both H; and n is 0, 1, 2, 3, 4, 5, 6, 7, 8, 9, 10, 11, 12, 13 or 14.

2. The compound of claim 1, wherein n is 1 or 5.

3. The compound of claim 1, wherein the double bond is in (Z) configuration.

4. The compound of claim 3, wherein the chiral center at C-3 has an R configuration.

5. The compound of claim 1, wherein the monosaccharide, disaccharide, trisaccharide, or polysaccharide is bound at the anomeric carbon via an α-glycosidic bond.

6. The compound of claim 1, wherein neither $R^1$ nor $R^2$ are H.

7. The compound of claim 1, wherein $R^1$ and $R^2$ are different monosaccharides.

8. The compound of claim 1, wherein $R^1$ and $R^2$ are the same monosaccharide.

9. The compound of claim 1, wherein the monosaccharide is a pentose sugar or a hexose sugar.

10. The compound of claim 9, wherein the monosaccharide is a hexose sugar selected from the group consisting of allose, altrose, glucose, mannose, gulose, iodose, galactose and talose.

11. The compound of claim 10, wherein the monosaccharide is glucose.

12. The compound of claim 1, wherein $R^1$ is glucose.

13. The compound of claim 1, wherein the disaccharide, trisaccharide, or polysaccharide comprises a pentose sugar, a hexose sugar, or a mixture thereof.

14. The compound of claim 13, wherein the disaccharide, trisaccharide, or polysaccharide comprises a hexose sugar selected from the group consisting of allose, altrose, glucose, mannose, gulose, iodose, galactose, talose, and a mixture of any two or more thereof.

15. The compound of claim 1, wherein $R^1$ is maltose or isomaltose.

16. A composition comprising the compound of claim 1, wherein the composition is selected from the group consisting of a personal care product, a pharmaceutical, a food product, and an agricultural formulation.

* * * * *